US010058301B2

(12) United States Patent
Tajima et al.

(10) Patent No.: US 10,058,301 B2
(45) Date of Patent: Aug. 28, 2018

(54) IMAGE ANALYSIS DEVICE, IMAGE ANALYSIS METHOD, AND PROGRAM

(71) Applicant: FUJIFILM Corporation, Tokyo (JP)

(72) Inventors: Takashi Tajima, Ashigarakami-gun (JP); Jun Enomoto, Ashigarakami-gun (JP); Yasufumi Oda, Ashigarakami-gun (JP); Takeshi Kuwabara, Ashigarakami-gun (JP); Daiki Harada, Ashigarakami-gun (JP); Yuichi Hosoi, Ashigarakami-gun (JP); Haruyasu Nakatsugawa, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 548 days.

(21) Appl. No.: 14/842,992

(22) Filed: Sep. 2, 2015

(65) Prior Publication Data

US 2016/0081648 A1    Mar. 24, 2016

(30) Foreign Application Priority Data

Sep. 24, 2014  (JP) ................................. 2014-193995
Aug. 11, 2015  (JP) ................................. 2015-158745

(51) Int. Cl.
    *A61B 6/00*           (2006.01)
(52) U.S. Cl.
    CPC .......... *A61B 6/5282* (2013.01); *A61B 6/4291* (2013.01); *A61B 6/5211* (2013.01)
(58) Field of Classification Search
    None
    See application file for complete search history.

(56) References Cited

U.S. PATENT DOCUMENTS 5,661,818 A *  8/1997  Gaborski ........... G06K 9/00449
                                                   378/164
6,269,176 B1 * 7/2001  Barski ....................... G06T 5/10
                                                   128/922
(Continued)

FOREIGN PATENT DOCUMENTS

JP    02-244881 A    9/1990
JP    06-014911 A    1/1994
(Continued)

*Primary Examiner* — Thomas R Artman
(74) *Attorney, Agent, or Firm* — Sughrue Mion, PLLC

(57) ABSTRACT

In an image analysis device, an image analysis method, and a non-transitory computer-readable recording medium, it is determined whether a radiographic image is captured by rocking a rocking imaging grid. The image analysis device includes: a radiographic image acquisition section; a dosage data acquisition section that acquires dosage data indicating, in a time-series manner, a dosage of radiation rays exposed to a specific position in an imaging area in a specific period; and a determining section that determines whether the dosage data has a first feature indicating a dosage variation as a plurality of radiation absorbing bodies and a radiation transmitting body disposed between adjacent radiation absorbing bodies pass through a space between the specific position and a radiation source, and determines that the radiographic image corresponding to the dosage data determined to have the first feature is a rocking grid use image captured by rocking a rocking imaging grid.

20 Claims, 8 Drawing Sheets

(56) References Cited

U.S. PATENT DOCUMENTS

| | | | |
|---|---|---|---|
| 7,479,969 B2* | 1/2009 | Behiels | G06K 9/4604 345/418 |
| 7,796,792 B2* | 9/2010 | Behiels | G06T 5/10 128/922 |
| 8,718,348 B2* | 5/2014 | Foos | G06T 5/005 382/128 |
| 9,579,076 B2* | 2/2017 | Tajima | H05G 1/44 |
| 9,629,601 B2* | 4/2017 | Tajima | A61B 6/542 |
| 9,780,128 B2* | 10/2017 | Tajima | H01L 27/14603 |
| 9,793,305 B2* | 10/2017 | Tajima | H01L 27/14603 |
| 2002/0015475 A1 | 2/2002 | Matsumoto et al. | |
| 2002/0191829 A1 | 12/2002 | Sasada | |
| 2006/0188146 A1* | 8/2006 | Behiels | G06K 9/4604 382/159 |
| 2007/0003125 A1* | 1/2007 | Behiels | G06T 5/10 382/132 |
| 2011/0033101 A1* | 2/2011 | Foos | G06T 5/005 382/132 |
| 2015/0030129 A1* | 1/2015 | Tajima | H05G 1/44 378/62 |
| 2015/0036802 A1* | 2/2015 | Tajima | A61B 6/4208 378/62 |
| 2015/0131784 A1* | 5/2015 | Tajima | A61B 6/4291 378/97 |
| 2015/0139398 A1* | 5/2015 | Tajima | G01T 1/2985 378/62 |
| 2016/0081648 A1* | 3/2016 | Tajima | A61B 6/5282 378/62 |
| 2016/0183908 A1* | 6/2016 | Hayashida | A61B 6/585 378/165 |
| 2016/0235384 A1* | 8/2016 | Enomoto | A61B 6/4291 |

FOREIGN PATENT DOCUMENTS

| | | |
|---|---|---|
| JP | 2000-083951 A | 3/2000 |
| JP | 2003-008885 A | 1/2003 |
| JP | 2003-260053 A | 9/2003 |

* cited by examiner

IMAGE ANALYSIS DEVICE, IMAGE ANALYSIS METHOD, AND PROGRAM

CROSS-REFERENCE TO RELATED APPLICATIONS

The present application claims priority under 35 U.S.C. § 119 to Japanese Patent Application No. 2014-193995, filed on Sep. 24, 2014 and Japanese Patent Application No. 2015-158745, filed on Aug. 11, 2015. Each of the above applications is hereby expressly incorporated by reference, in its entirety, into the present application.

BACKGROUND OF THE INVENTION

1. Field of the Invention

The present invention relates to an image analysis device, an image analysis method, and a non-transitory computer-readable recording medium that stores an image analysis program that analyze a radiographic image acquired by imaging a photographic subject.

2. Description of the Related Art

In the related art, when capturing a radiographic image of a photographic subject by using radiation rays that pass through the photographic subject, especially, if the thickness of the photographic subject is large, the radiation rays are scattered inside the photographic subject, and the contrast of the acquired radiographic image may deteriorate due to the scattered radiation rays (hereinafter, referred to as scattered rays). Thus, when capturing the radiographic image, a scattered ray removal grid (hereinafter, referred to as a grid) is disposed between the photographic subject and a radiation detector that detects radiation rays to obtain a radiographic image so that the radiation detector is not irradiated with scattered rays before imaging, in some cases. If the imaging is performed using the grid, the radiation detector is not easily irradiated with the radiation rays scattered by the photographic subject, and thus, it is possible to enhance the contrast of the radiographic image.

On the other hand, if the imaging is performed using the grid, a photographic subject image and a stripe pattern (grid stripe) corresponding to the grid are included in the radiographic image, which deteriorates the image quality of the image. Accordingly, a process of removing a grid stripe from a radiographic image captured using a grid is known (see JP2003-260053A, JP2000-083951A, JP2003-008885A, and JP1994-014911A (JP-H06-014911A)). Further, the grid stripe is generated when a stationary grid for performing stationary imaging is used, and is not generated in the radiographic image when a rocking grid (Bucky-Potter grid) for rocking imaging is used. Thus, when the rocking grid is used, it is possible to obtain a radiographic image with high image quality without a grid stripe, without performing the above-mentioned grid stripe suppression process.

In this regard, since a lead material or the like that does not transmit radiation rays, and an inter-space material made of aluminum, fiber or the like that transmits radiation rays are alternately disposed in a fine grating density of about 4.0 lines/mm, for example, the grid has a large weight. In portable imaging performed in a hospital room or the like, it is necessary to dispose a grid between a patient who is on a bed and a radiation detector. Accordingly, the weight of the grid causes an increased workload of a grid mounting operation to a photographer, and increased burdens of the patient in imaging. Further, in the case of a convergence type grid, there is a concern that density unevenness occurs in a radiographic image due to oblique incidence of radiation rays.

Thus, a process of performing capturing of a radiographic image without using a grid and assigning an image quality improvement effect acquired by removing scattered rays by the grid to the radiographic image using image processing has been proposed (see JP1990-244881A (JP-H02-244881A)). According to the technique disclosed in JP1990-244881A (JP-H02-244881A), a photographic subject image is classified for each pixel of the photographic subject image according to a body thickness depending on an image signal, a total scattered ray distribution generated by a photographic subject having each classified body thickness is calculated, and the total scattered ray distribution is subtracted from the radiographic image to obtain a radiographic image in which a component of scattered rays is removed. According to the technique disclosed in JP1990-244881A (JP-H02-244881A), since the grid is not necessary in imaging, it is possible to reduce the burden of the patient in imaging, and to prevent deterioration of image quality due to density unevenness and a grid stripe.

However, in a radiography system capable of acquiring three types of radiographic images of a radiographic image captured using a stationary grid, a radiographic image captured using a Bucky-Potter grid, and a radiographic image captured without using a grid, when a process of removing a grid stripe with respect to all of the acquired radiographic images is performed, a grid stripe suppression process is performed even with respect to the radiographic image captured without using the grid. Contrarily, when a scattered ray suppression process is performed, the scattered ray suppression process is performed even with respect to the radiographic image captured using the grid. In this way, if an unnecessary process in a specific radiographic image is performed with respect to the radiographic image, the image quality of the radiographic image greatly deteriorates, and thus, it is difficult to perform diagnosis with high efficiency.

Thus, according to JP2003-260053A and JP2000-083951A, for example, a grid is retained in a frame-shaped retention section in which a protrusion portion is disposed at a different position according to a grid type, and a micro-switch is provided at a position on a device that faces a protrusion portion of the grid, and the micro-switch is turned on according to the grid type. JP2003-260053A and JP2000-083951A disclose a technique for determining the presence or absence of the grid, or the type thereof, and performing image processing depending on the presence or absence of the grid, or the type thereof, using the above configuration. Further, JP2003-260053A and JP2000-083951A disclose a technique for detecting values of parameters that are changed due to a load applied to a motor that rocks a grid to determine the presence or absence of the grid, or the weight thereof.

SUMMARY OF THE INVENTION

However, there is a possibility that the techniques disclosed in JP2003-260053A and JP2000-083951A cannot be employed according to the circumstances necessary for an imaging system, an imaging purpose or the like. Accordingly, in order to meet various requirements depending on the imaging system or the imaging purpose, a technique for determining the type of the grid is necessary, in addition to the techniques disclosed in JP2003-260053A and JP2000-083951A.

In order to solve the above-mentioned problems, an advantage of some aspects of the invention is to provide an image analysis device, an image analysis method for determining whether a radiographic image is captured by rocking a rocking imaging grid for removing scattered rays, and a non-transitory computer-readable recording medium that stores an image analysis program for determining whether a radiographic image is captured by rocking a rocking imaging grid for removing scattered rays.

According to an aspect of the invention, there is provided an image analysis device including a radiographic image acquisition section that acquires a radiographic image acquired by radiography, a dosage data acquisition section that acquires dosage data indicating, in a time-series manner, a dosage of radiation rays exposed to a specific position in an imaging area corresponding to the radiographic image in a specific period including an imaging period of the radiographic image, and a determining section that determines whether the dosage data has a first feature indicating a dosage variation as a plurality of radiation absorbing bodies and a radiation transmitting body disposed between adjacent radiation absorbing bodies pass through a space between the specific position and a radiation source used for the radiography, and determines that the radiographic image corresponding to the dosage data determined to have the first feature is a rocking grid use image captured by rocking a rocking imaging grid for removing scattered rays.

According to another aspect of the invention, there is provided an image analysis method that is executed in an image analysis device, including the steps of: acquiring a radiographic image acquired by radiography; acquiring dosage data indicating, in a time-series manner, a dosage of radiation rays exposed to a specific position in an imaging area corresponding to the radiographic image in a specific period including an imaging period of the radiographic image; and determining whether the dosage data has a first feature indicating a dosage variation as a plurality of radiation absorbing bodies and a radiation transmitting body disposed between adjacent radiation absorbing bodies pass through a space between the specific position and a radiation source used for the radiography, and determining that the radiographic image corresponding to the dosage data determined to have the first feature is a rocking grid use image captured by rocking a rocking imaging grid for removing scattered rays.

According to still another aspect of the invention, there is provided a non-transitory computer-readable recording medium that stores a radiographic image processing program that causes a computer to execute the above-described image analysis method.

The "imaging period" means a period that substantially contributes to the formation of an image signal corresponding to a radiographic image in a period when radiation rays are emitted to an imaging target for the radiographic image. For example, the imaging period may be a period when electric charges are accumulated in each pixel for formation of a radiographic image in a radiation detector in which pixels that accumulate electric charges according to the amount of incidence of radiation rays are arranged in a two-dimensional matrix form.

Further, it is sufficient if the "specific period" is a period including at least a part of the imaging period. In addition, the "specific period" is set as a period longer than a period necessary when a radiation absorbing body of a grid passes through a space between a specific position and a radiation source at least two times. For example, it is preferable that the specific period is set as a period after the time when a dosage of radiation rays in dosage data is equal to or greater than a threshold value capable of determining irradiation with radiation rays, which is a period longer than the period necessary when the radiation absorbing body layer of the grid passes through the space between the specific position and the radiation source at least two times. In this case, the necessary period is calculated from an expected pitch of a radiation grid and an expected rocking speed of the grid.

Further, the "first feature" refers to a feature for specifying that a scattered ray removing grid in which a radiation absorbing body and a radiation transmitting body respectively having specific widths are alternately arranged moves in a space between a specific position on a detection surface of a radiation detector in an imaging region and a radiation source. As long as the first feature indicates a feature of dosage data variation that appears as plural radiation absorbing bodies and radiation transmitting bodies disposed between adjacent radiation absorbing bodies pass through a space between a specific position and a radiation source used for the radiography, the first feature may be specified by any method.

In the image analysis device according to the aspect of the invention, the determining section may determine whether the dosage data has the first feature, using a feature that the dosage data has adjacent sine wave shapes having a uniform amplitude as the first feature.

The "dosage data has adjacent sine wave shapes having a uniform amplitude" includes a case where the amplitudes of the adjacent sine wave shapes are uniform and a case where the amplitudes thereof are substantially uniform. Further, in the adjacent sine wave shapes, when an amplitude in a positive direction is uniform and an amplitude in a negative direction is uniform, the amplitudes in the positive direction and the negative direction may be the same, or may be different from each other. Further, the "sine wave shape" includes a strict sine wave, and also includes a shape considered as an approximately sine wave shape.

Further, the determining section may use any method capable of determining whether the dosage data has the "feature having adjacent sine wave shapes having a uniform amplitude". For example, the determination section may use a method for calculating a curve fitted from plural dosage values of dosage data, comparing the calculated curve with adjacent sine wave shapes having a uniform amplitude, and determining whether the calculated curve has the adjacent sine wave shapes having the uniform amplitude. It is preferable that plural samples in which an appropriate cycle and an appropriate amplitude are set according to an expected movement speed of a Bucky-Potter grid in a movement direction, the amount of radiation absorption of a radiation transmitting body, the width of the radiation transmitting body in the movement direction, the amount of radiation absorption of a radiation absorbing body, the width of the radiation absorbing body in the movement direction, and the like are provided as the adjacent sine wave shapes having the uniform amplitude used for comparison.

Further, in the image analysis device according to the aspect of the invention, the determining section may determine whether the dosage data has the first feature, using a feature that the dosage data alternately has a positive maximum value due to passage of each radiation transmitting body and a minimum value which is zero or greater due to passage of each radiation absorbing body at a uniform interval as the first feature.

Further, in the image analysis device according to the aspect of the invention, the determining section may use any method capable of determining that the dosage data has the "feature that the dosage data alternately has a positive maximum value due to passage of the radiation transmitting body and a minimum value which is zero or greater due to passage of the radiation absorbing body at a uniform interval". For example, it is preferable to use a method for calculating a curve fitted from plural dosage values of dosage data, detecting a maximum value and a minimum value in a time-series manner, and determining whether a positive maximum value and a minimum value which is equal to or greater than zero are alternately repeated.

Further, in the image analysis device according to the aspect of the invention, the determining section may determine that the radiographic image corresponding to the dosage data determined not to have the first feature is any one of a stationary grid use image captured with a stationary imaging grid for removing scattered rays being stationary and a grid non-use image captured with the grid for removing the scattered rays not being used.

The "grid non-use image captured with the grid for removing the scattered rays not being used" refers to a radiographic image acquired by radiography in a state where both the rocking imaging grid for removing the scattered rays and the stationary imaging grid are not positioned between a radiation source and a radiation detector in imaging.

Further, in the image analysis device according to the aspect of the invention, the determining section may determine whether the radiographic image has a second feature indicating that the radiographic image includes an image of a stationary imaging grid, determine that the radiographic image determined to have the second feature is a stationary grid use image, and determine that the radiographic image corresponding to the dosage data determined not to have the first feature and determined not to have the second feature is a grid non-use image.

Further, the image analysis device according to the aspect of the invention may further include a grid stripe suppressing section that suppresses a frequency component corresponding to the image indicating the stationary imaging grid included in the stationary grid use image from the stationary grid use image.

Further, the image analysis device according to the aspect of the invention may further include a scattered ray suppressing section that performs a scattered ray component suppression process of generating a scattered ray image indicating a scattered ray component in each position of the grid non-use image from the grid non-use image, and subtracting the scattered ray image from the grid non-use image.

Further, in the image analysis device according to the aspect of the invention, the determining section may determine whether rocking grid information indicating that the radiographic image is captured by rocking the rocking imaging grid is included in imaging instruction information indicating an imaging instruction of the radiographic image, determine the rocking grid use image when it is determined that the rocking grid information is included in the imaging instruction information based on the rocking grid information of the imaging instruction information, and determine the rocking grid use image by determining whether the dosage data has the first feature when it is determined that the rocking grid information is not included in the imaging instruction information.

The "imaging instruction information" refers to information transmitted to an imaging operator from a doctor for instruction of imaging, which includes information for specifying an imaging target and image inspection performed with respect to the imaging target. For example, the imaging instruction information includes basic information relating to an imaging target such as a name, gender and age of a patient, an instruction of radiography, an imaging range, an imaging direction, imaging conditions, and the like.

Further, in the image analysis device according to the aspect of the invention, the determining section may add determination information indicating whether it is determined that the radiographic image is the rocking grid use image as additional information with respect to the radiographic image.

According to the invention, it is possible to appropriately determine whether a radiographic image is an image captured by rocking a rocking imaging grid for removing scattered rays.

DESCRIPTION OF THE PREFERRED EMBODIMENTS

Hereinafter, embodiments of the invention will be described with reference to the accompanying drawings.

Figure 1:
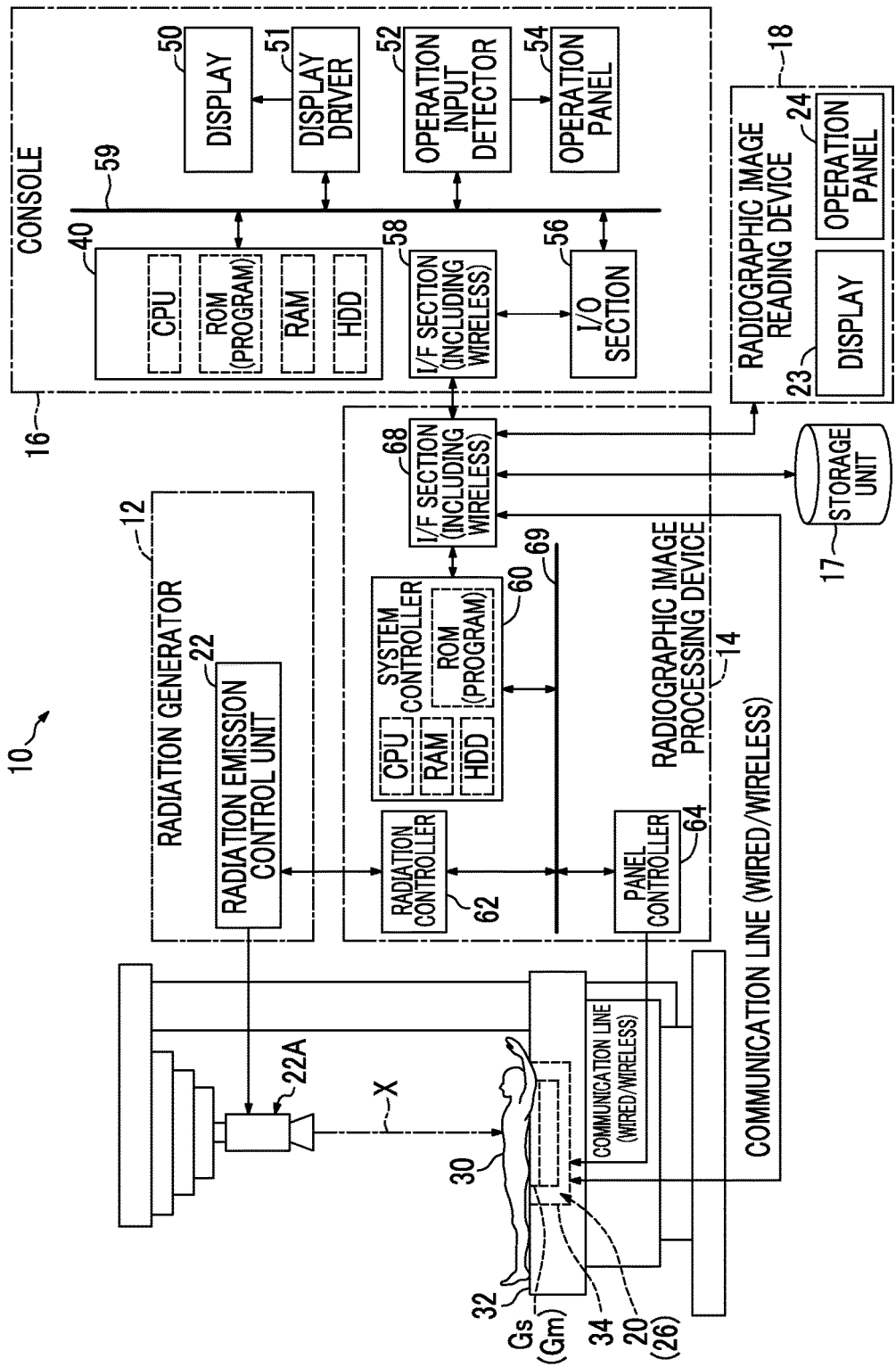
FIG. 1 is a schematic block diagram illustrating a configuration of a radiation imaging system to which a radiographic image processing device according to an embodiment of the invention is applied.

First, a schematic configuration of the entirety of a radiation imaging system provided with a radiographic image processing device according to an embodiment of the invention will be described. FIG. 1 is a schematic configuration diagram illustrating an outline of an overall configuration of an example of a radiation imaging system according to an embodiment of the invention. A radiation imaging system 10 according to this embodiment has a function of detecting irradiation starting (imaging starting) of radiation rays by an electronic cassette 20.

The radiation imaging system 10 according to this embodiment has a function of capturing a radiographic image by an operation of a doctor, a radiologist, or the like based on an instruction (imaging menu) input from an external system (for example, a radiology information system) through a console 16.

Further, the radiation imaging system 10 according to this embodiment has a function of displaying the captured radiographic image on a display 50 of the console 16 or in a radiographic image reading device 18 to allow a doctor, a radiologist, or the like to read the radiographic image.

The radiation imaging system 10 according to this embodiment includes a radiation generation device 12, a radiographic image processing device 14, the console 16, a storage unit 17, the radiographic image reading device 18, and the electronic cassette 20.

The radiation generation device 12 includes a radiation exposing control unit 22. The radiation exposing control unit 22 has a function of irradiating an imaging target portion of an examinee 30 on a photographing stand 32 with radiation rays X from a radiation source 22A based on the control of a radiation controller 62 of the radiographic image processing device 14.

The electronic cassette 20 retained by a retaining section 34 in the photographing stand 32 is irradiated with the radiation rays X that pass through the examinee 30. The electronic cassette 20 has a function of generating electrical charges depending on the dosage of the radiation rays X that pass through the examinee 30, and generating and outputting image information indicating a radiographic image based on the generated electrical charges. The electronic cassette 20 according to this embodiment includes a radiation detector 26.

Further, on a photographic subject side of the radiation detector 26, a grid Gm and a grid Gs that prevents the radiation rays scattered in the examinee 30 from entering the radiation detector 26 are provided so as to be freely taken in and out. In this embodiment, the grid Gm is a rocking imaging grid, and the grid Gs is a stationary imaging grid.

In this embodiment, image information indicating a radiographic image output by the electronic cassette 20 is input to the console 16 through the radiographic image processing device 14. The console 16 of this embodiment has a function of controlling the radiation generation device 12 and the electronic cassette 20 using a photographic menu, a variety of information, or the like acquired from an external system (RIS) or the like through a local area network (LAN) or the like. Further, the console 16 of this embodiment has a function of performing transmission/reception of a variety of information including image information about a radiographic image between the console 16 and the radiographic image processing device 14, and has a function of performing transmission/reception of a variety of information between the console 16 and the electronic cassette 20.

The console 16 of this embodiment is configured by a server and a computer, and includes a controller 40, a display driver 51, a display 50, an operation input detector 52, an operation panel 54, an I/O section 56, and an I/F section 58.

The controller 40 has a function of controlling an overall operation of the console 16, and includes a central processing unit (CPU), a read only memory (ROM), a random access memory (RAM), and a hard disk drive (HDD). The CPU has a function of controlling the overall operation of the console 16, and various programs or the like including a control program used in the CPU are stored in the ROM in advance. The RAM has a function of temporarily storing a variety of data, and the HDD has a function of storing and retaining a variety of data.

The display driver 51 has a function of controlling display of a variety of information on the display 50. The display 50 of this embodiment has a function of displaying a photographing menu, a captured radiographic image, or the like. The operation input detector 52 has a function of detecting an operation state with respect to the operation panel 54. The operation panel 54 is used when a doctor, a radiologist, or the like inputs an operation instruction relating to capturing of a radiographic image. In this embodiment, for example, the operation panel 54 includes a touch panel, a touch pen, plural keys, a mouse, and the like. When the operation panel 54 is configured by the touch panel, the display 50 may have a function of the touch panel.

Further, the I/O section 56 and the I/F section 58 have a function of transmitting/receiving a variety of information between the radiographic image processing device 14 and the radiation generation device 12 through wireless communication. Further, the I/O section 56 and the I/F section 58 have a function of transmitting/receiving a variety of information such as image information between the I/O section 56 and the I/F section 58 and the electronic cassette 20 through wireless communication.

The controller 40, the display driver 51, the operation input detector 52, and the I/O section 56 are connected to each other to exchange information or the like through a bus 59 such as a system bus or a control bus. Accordingly, the controller 40 may perform control of display of a variety of information on the display 50 through the display driver 51, and may perform control of transmission/reception of a variety of information with respect to the radiation generation device 12 and the electronic cassette 20 through the I/F section 58.

The radiographic image processing device 14 of this embodiment has a function of controlling the radiation generation device 12 and the electronic cassette 20 based on an instruction from the console 16, and has a function of controlling storage of a radiographic image received from the electronic cassette 20 into the storage unit 17 and display of the radiographic image on the display 50 of the console 16 or the radiographic image reading device 18.

The radiographic image processing device 14 of this embodiment includes a system controller 60, a radiation controller 62, a panel controller 64, and an I/F section 68.

The system controller 60 has a function of controlling the entirety of the radiographic image processing device 14, and has a function of controlling the radiation imaging system 10. The system controller 60 includes a CPU, a ROM, a RAM, and an HDD. The CPU has a function of controlling the entirety of the radiographic image processing device 14 and an operation of the radiation imaging system 10. Various programs or the like including a control program used in the CPU are stored in the ROM in advance. The RAM has a function of temporarily storing a variety of data. The HDD has a function of storing and retaining a variety of data. The radiation controller 62 has a function of controlling the radiation exposing control unit 22 of the radiation generation device 12 based on an instruction of the console 16. The panel controller 64 has a function of receiving information from the electronic cassette 20 in a wireless or wired manner.

The system controller 60, the radiation controller 62, and the panel controller 64 are connected to each other to exchange information or the like through a bus 69 such as a system bus or a control bus.

The storage unit 17 has a function of storing a captured radiographic image and information relating to the radiographic image. An HDD or the like may be used as the storage unit 17, for example.

Further, the radiographic image reading device 18 is a device that has a function for reading a captured radiographic image by a user, and is not particularly limited. A so-called image reading viewer, console, tablet terminal, or the like may be used as the radiographic image reading device 18. The radiographic image reading device 18 of this embodiment is configured by a personal computer, and includes a CPU, a ROM, a RAM, an HDD, a display driver, a display 23, an operation input detector, an operation panel 24, an I/O section, and an I/F section, similar to the console 16 or the radiographic image processing device 14. In FIG. 1, for ease of illustration, only the display 23 and the operation panel 24 among the components are shown, and the others are not shown.

Figure 2:
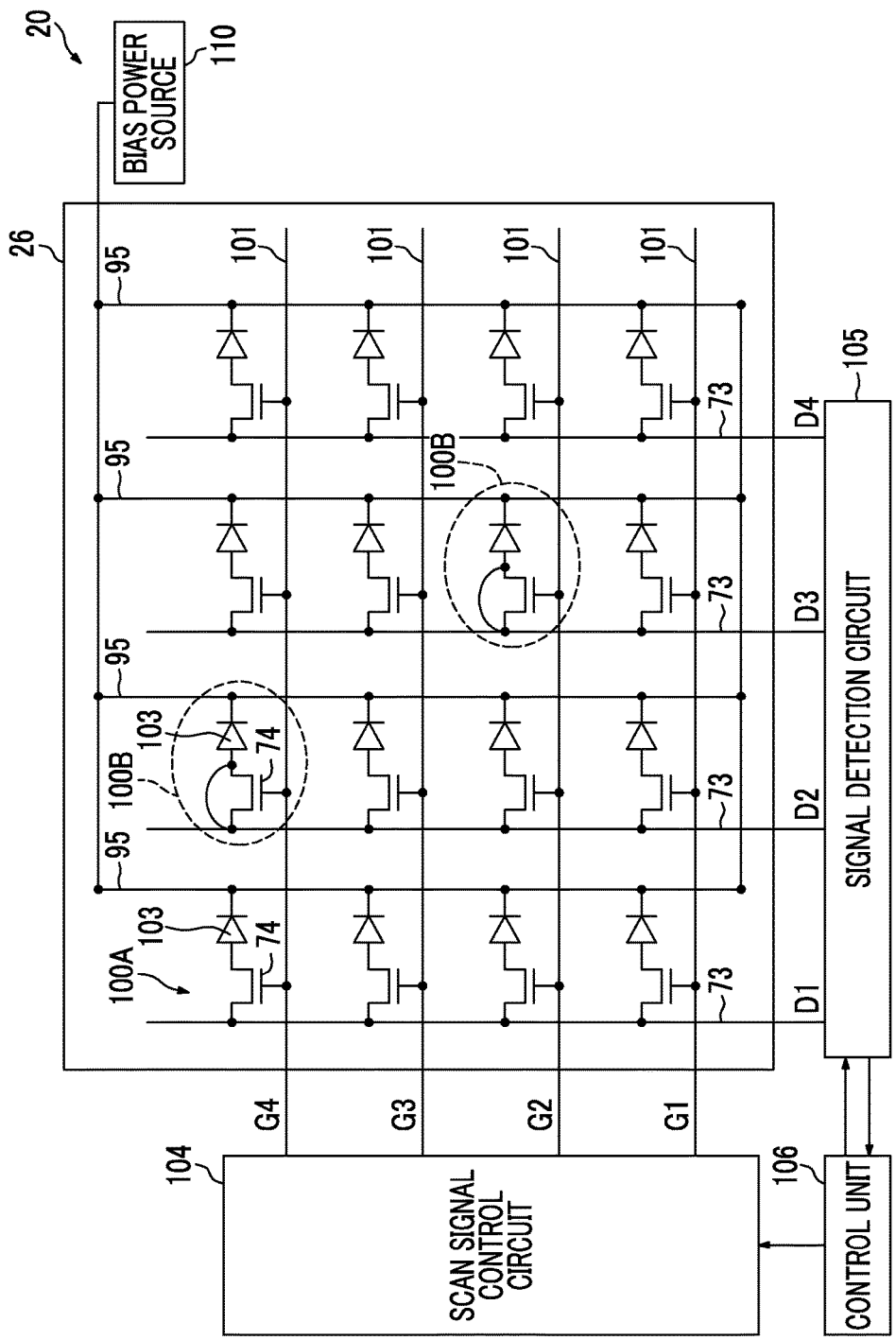
FIG. 2 is a configuration diagram illustrating an example of an overall configuration of an electronic cassette according to a first embodiment.

Next, a schematic configuration of the electronic cassette 20 will be described. In this embodiment, a case where the invention is applied to the radiation detector 26 of an indirect conversion type for converting radiation rays such as X-rays into light once and converting the converted light into electrical charges will be described. In this embodiment, the electronic cassette 20 includes the radiation detector 26 of an indirect conversion type. In FIG. 2, a scintillator that converts the radiation rays into light is not shown.

Plural pixels 100 configured by a sensor section 103 that receives light to generate electrical charges and stores the generated electrical charges, and a TFT switch 74 which is a switching element for reading the accumulated electrical charges in the sensor section 103 are arranged in a matrix form in the radiation detector 26. In this embodiment, due to irradiation with light converted by the scintillator, the electrical charges are generated in the sensor section 103.

The plural pixels 100 are arranged in the matrix form in one direction (a gate wiring direction in FIG. 2) and in a cross direction with respect to the gate wiring direction (a signal wiring direction in FIG. 2). In FIG. 2, the arrangement of the pixels 100 is simplified. For example, the pixels 100 of 1024×1024 are arranged in the gate wiring direction and the signal wiring direction.

In this embodiment, a radiation imaging pixel 100A and a radiation detecting pixel 100B among the plural pixels 100 are determined in advance. In FIG. 2, the radiation detecting pixel 100B is surrounded by a broken line. The radiation imaging pixel 100A is used for detection of radiation rays and generation of an image indicated by the radiation rays. The radiation detecting pixel 100B is a pixel used for detection of radiation rays for detecting irradiation starting of the radiation rays or the like, and is a pixel that outputs electrical charges even in an electrical charge accumulation period (details will be described later).

Further, in the radiation detector 26, plural gate wirings 101 for turning on/off the TFT switch 74 and plural signal wirings 73 for reading electrical charges accumulated in the sensor section 103 are provided to intersect each other on a substrate (not shown). In this embodiment, one signal wiring 73 is provided in each pixel column in one direction, and one gate wiring 101 is provided in each pixel row in a cross direction. For example, when the pixels 100 of 1024×1024 are arranged in the gate wiring direction and the signal wiring direction, the signal wirings 73 of 1024 and the gate wirings 101 of 1024 are provided, respectively.

Further, in the radiation detector 26, common electrode wirings 95 are provided in parallel with the respective signal wirings 73. The common electrode wirings 95 are connected in parallel between first ends and second ends, and the first ends are connected to a bias power source 110 that supplies a predetermined bias voltage. The sensor section 103 is connected to the common electrode wiring 95, and is supplied with the bias voltage through the common electrode wiring 95.

A control signal for switching each TFT switch 74 flows in the gate wiring 101. As the control signal flows in each gate wiring 101 in this way, each TFT switch 74 is switched.

An electric signal depending on electric charges accumulated in each pixel 100 flows in the signal wiring 73 according to a switching state of the TFT switch 74 of each pixel 100. Specifically, an electric signal depending on electrical charges accumulated as the TFT switch 74 of any one of the pixels 100 connected to the signal wiring 73 is turned on flows in each signal wiring 73.

A signal detection circuit 105 that detects an electric signal flowing in each signal wiring 73 is connected to each signal wiring 73. Further, a scan signal control circuit 104 that outputs a control signal for turning on/off the TFT switch 74 to each gate wiring 101 is connected to each gate wiring 101. In FIG. 2, each of the signal detection circuit 105 and the scan signal control circuit 104 is simply shown as one element, but for example, plural signal detection circuits 105 and plural scan signal control circuits 104 are provided, and the signal wirings 73 or the gate wirings 101 of a predetermined number (for example, 256) are connected thereto. For example, when 1024 signal wirings 73 and 1024 gate wirings 101 are provided, four scan signal control circuits 104 are provided for connection of 256 gate wirings 101, and four signal detection circuit 105 are provided for connection of 256 signal wirings 73.

The signal detection circuit 105 includes therein a known amplifier circuit that amplifies an input electric signal for each signal wiring 73. The signal detection circuit 105 amplifies the electric signal input from each signal wiring 73 by the amplifier circuit, and converts the electric signal into a digital signal by an analog-digital converter (ADC).

A control unit 106 that performs a predetermined process such as noise removal with respect to the digital signal converted in the signal detection circuit 105, outputs a control signal indicating a signal detection timing to the signal detection circuit 105, and outputs a control signal indicating a scan signal output timing to the scan signal control circuit 104 is connected to the signal detection circuit 105 and the scan signal control circuit 104.

The control unit 106 is configured by a microcomputer, and includes a central processing unit (CPU), a ROM, a RAM, and a non-volatile storage unit formed by a flash memory or the like. The control unit 106 causes the CPU to execute a program stored in the ROM, to thereby perform control for capturing a radiographic image. Further, the control unit 106 performs a process (interpolation process) of interpolating image data on the respective radiation detecting pixels 100B with respect to image data subjected to the above-described predetermined process to generate an image indicated by irradiation with radiation rays. That is, the control unit 106 interpolates the image data about the respective radiation detecting pixels 100B based on the image data subjected to the above-described predetermined process, to thereby generate an image indicated by irradiation with radiation rays.

The electronic cassette 20 detects an electric signal (electrical charges information) of the signal wiring 73 (at least one of D2 and D3 in FIG. 2, for example, D2) connected to the radiation detecting pixel 100B by the amplifier circuit 120 of the signal detection circuit 105, and the control unit 106 compares a value of a digital signal converted by the signal detection circuit 105 with a predetermined detection threshold value TH1, and detects whether the value of the digital signal is equal to or greater than the threshold value to detect whether irradiation with radiation rays is performed. That is, the electronic cassette 20 performs the detection relating to the irradiation with the radiation rays without a control signal from an external device (for example, the radiographic image processing device 14). The detection of whether the irradiation with the radiation rays is performed using the control unit 106 may be performed based on a predetermined condition such as the number of times of detection, instead of the comparison with the detection threshold value.

Here, in this embodiment, the "detection" of the electric signal refers to sampling of the electric signal. Hereinafter, data indicating time-series electric signals (pixel signals) monitored in the radiation detecting pixel 100B is referred to as dosage data. In this embodiment, the radiation detecting pixel 100B detects irradiation starting of radiation rays, and then, continues the detection of the electric signal (electrical charges information) output from the radiation detecting pixel 100B. Further, although described later in detail, dosage data in a specific period including an imaging period is acquired.

As long as dosage data on radiation rays can be acquired, an arbitrary detection method and a detection pixel with an arbitrary configuration may be employed. For example, in order to monitor dosage data on radiation rays, employable configurations (1) to (6) are shown as follows.

(1) A pixel that is arbitrarily selected from radiation imaging pixels (two-dimensional array) is set as an exclusive radiation detecting pixel. In this case, the radiation imaging pixel and the radiation detecting pixel are formed in the same shape.

(2) A pixel that is arbitrarily selected from radiation imaging pixels (two-dimensional array) is also able to perform radiation detection. That is, a part of the pixels is set as a pixel for radiographic image capturing and radiation detection. For example, the selected pixel may have a configuration in which a sensor section is divided into two parts, and is dividedly used in the radiographic image capturing and the radiation detection. Further, for example, the selected pixel may have a configuration in which a TFT switch is additionally provided and radiation rays are detected based on a leakage current of the additionally provided TFT switch.

(3) An exclusive radiation detecting sensor is arbitrarily disposed between pixels (for example, in a gap between the pixels) of the radiation imaging pixels (two-dimensional array).

In the methods (2) and (3), only the selected pixel (selected gap) of a radiation detector used in these methods may have such a structure. Further, structures of the sensor section and the TFT switch may be repetitively patterned, and only the selected pixel may be connected for extraction of electrical charges.

(4) Radiation imaging pixels (two-dimensional array) and gaps thereof have a normal configuration, and separate detection means is provided. As a detection method, for example, bias current detection, gate current detection, and leakage current detection of a radiation detector, or the like may be used.

(5) Radiation imaging pixels (two-dimensional array) and gaps thereof have a normal configuration, and separate detection means is not provided. Instead, a controller for radiographic image capturing may be used for detection. As a detection method, for example, leakage current detection or the like may be used.

Any method of (1) to (5) corresponds to a case where a sensor that generates electrical charges (electric signal) according to a dosage of radiation rays radiated in the radiation detector is provided. These methods are not limiting, and a sensor may be provided outside a radiation detector as in (6). The sensor inside the radiation detector and the sensor outside the radiation detector are collectively referred to as a radiation sensor.

(6) A radiation detecting sensor is provided outside a radiation detector. For example, the radiation detecting sensor is provided on a bottom surface of the radiation detector which is not irradiated with radiation rays.

Further, in any method of (1) to (6), radiation rays may be detected when a gate of the TFT switch is turned on, or when the gate is turned off.

In addition, as the configuration and arrangement of the radiation detector 26 of the electronic cassette 20 of this embodiment, an arbitrary configuration may be employed in a range where the acquisition of dosage data and the generation of image information are possible.

Figure 3:
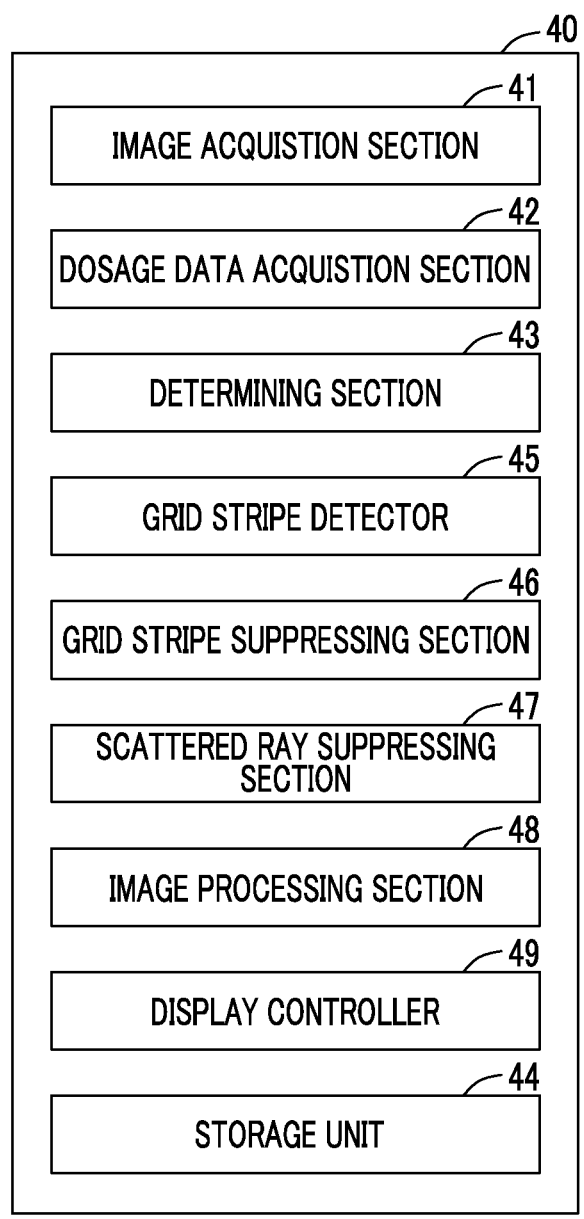
FIG. 3 is a schematic block diagram illustrating a configuration of a radiographic image processing device according to an embodiment of the invention.

The controller 40 of the console 16 further includes a function as an image analysis device, in addition to the function of controlling the overall operation of the console 16. The controller 40 (image analysis device) executes an image analysis program of an embodiment of the invention by hardware such as a CPU, a ROM, a RAM, and an HDD, to thereby function as an image acquisition section 41, a dosage data acquisition section 42, a determining section 43, a grid stripe detector 45, a grid stripe suppressing section 46, a scattered ray suppressing section 47, an image processing section 48, a display controller 49, and a storage section 44 as shown in FIG. 3.

When an operation input is detected by the operation input detector 52 in the console 16, the image acquisition section 41 acquires a radiographic image depending on the operation input. The radiographic image is an image acquired by performing an interpolation process in the control unit 106 with respect to an image signal detected by the radiation imaging pixel 100A in the radiation detector 26.

The dosage data acquisition section 42 acquires dosage data indicating, in a time-series manner, a dosage of radiation rays exposed to a position (specific position) of the radiation detecting pixel 100B as shown in FIG. 2 in an imaging area corresponding to a radiographic image, in a specific period including an imaging period of the radiographic image. The dosage data in radiation imaging and the radiographic image captured by the radiation imaging (radiographic image corresponding to the dosage data) are associated with each other to be stored in the storage unit 17.

The "specific period" represents a period including at least a part of the imaging period. Further, the "specific period" is set as a period longer than a period necessary when a radiation absorbing body of a grid passes through a space between a specific position and a radiation source at least two times. For example, it is preferable that the specific period is set by calculating a period after the time when the dosage in the dosage data is equal to or greater than a threshold value capable of determining irradiation with radiation rays, which is a period longer than the period necessary when the radiation absorbing body layer of the grid passes through the space between the specific position and the radiation source at least two times, from an expected pitch of the radiation grid and an expected rocking speed of the grid. In this embodiment, dosage data in a period from imaging starting t0 of a radiographic image to imaging ending is detected by the radiation detecting pixel 100B and is stored in the storage unit 17, and then, is acquired by the dosage data acquisition section 42 of the controller 40 from the storage unit 17.

The determining section 43 determines whether dosage data has a first feature indicating a dosage variation as plural radiation absorbing bodies and radiation transmitting bodies disposed between adjacent radiation absorbing bodies pass through a space between a specific position and a radiation source used for radiography, and determines that a radiographic image corresponding to dosage data determined to have the first feature (which will be described later) is a rocking grid use image captured by rocking the grid Gm for removing scattered rays.

Further, the determining section 43 according to this embodiment determines that a radiographic image corresponding to dosage data determined not to have the first feature is any one of a stationary grid use image captured with the grid Gs for removing scattered rays being stationary and a grid non-use image captured with the grid for removing the scattered rays not being used.

Further, the determining section 43 determines whether a radiographic image has a second feature that the radiographic image includes a grid stripe (stationary grid image) due to a stationary grid based on the presence or absence of the grid stripe in the radiographic image detected by a grid stripe detector 45 (which will be described later), determines that a radiographic image determined to have the second feature is a stationary grid use image, and determines that the radiographic image corresponding to the dosage data determined not to have the first feature, which is a radiographic image determined not to have the second feature, is a grid non-use image.

Further, the determining section 43 adds determination information indicating whether it is determined that the radiographic image is the rocking grid use image in the process of determining whether the radiographic image is the rocking grid use image as additional information with respect to the radiographic image. After the process of determining whether the radiographic image is the rocking grid use image is executed, the respective sections of the determining section 43, the grid stripe detector 45, the grid stripe suppressing section 46, the scattered ray suppressing section 47, the display controller 49, and the like determine a necessary process or an unnecessary process for the rocking grid use image, with reference to the additional information of the radiographic image as necessary.

As described above, the determining section 43 according to this embodiment determines that the radiographic image that has the first feature is the rocking grid use image, determines that the radiographic image that has the second feature is the stationary grid use image, and determines that the radiographic image that does not have the first and second features is the grid non-use image. That is, the determining section 43 can determine the presence or absence of usage of the grid with respect to the radiographic image, and the type of the grid used in the radiographic image, based on the presence or absence of the first feature and the second feature of the radiographic image. The determining section 43 may perform the process of determining the rocking grid use image based on the presence or absence of the first feature (a process of determining the presence or absence of rocking of the grid Gm when capturing the radiographic image), and the process of determining the stationary grid use image based on the presence or absence of the second feature, in an arbitrary order.

Here, concepts of dosage data acquired by the radiation detecting pixel 100B when capturing a radiographic image by the electronic cassette 20 with the above-described configuration and determination of a rocking grid use image using the dosage data will be described with reference to FIGS. 4 and 5.

Figure 4:
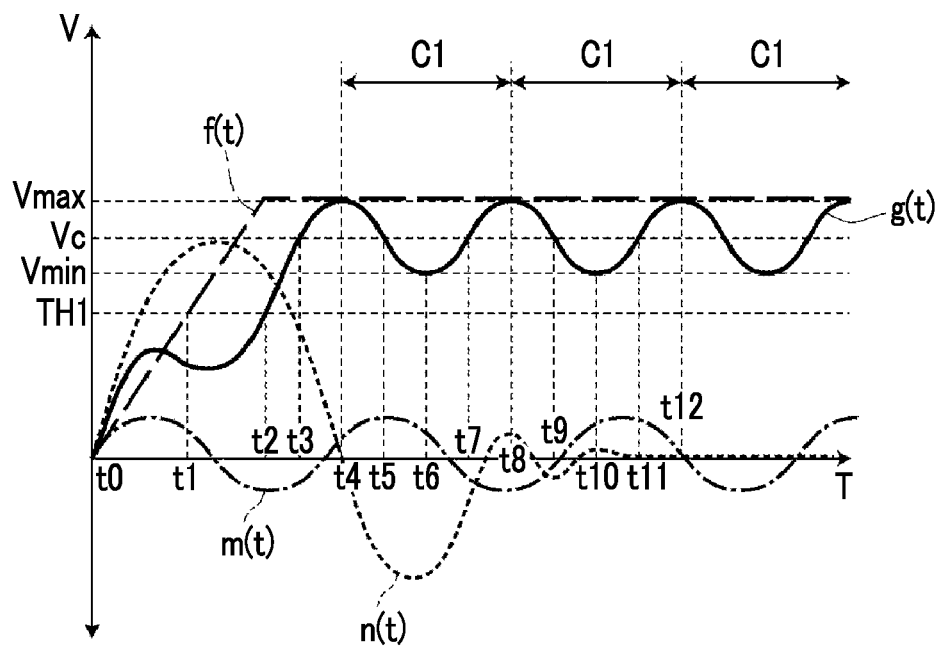
FIG. 4 is a diagram illustrating a time-series graph indicating dosage data.

FIG. 4 shows an example of dosage data acquired by the radiation detecting pixel 100B. FIG. 4 is a time-series graph in which a transverse axis represents a time axis and a longitudinal axis represents a pixel signal value. If irradiation with radiation rays is performed, an electric signal Di increases and is changed over time, and thus, may be expressed as a function of time t. The radiation detector 26 of this embodiment detects irradiation starting of radiation rays according to whether the electric signal Di exceeds a detection threshold value. In FIG. 4, dosage data when irradiation with radiation rays is performed in a state where a grid is not used is expressed as f(t), dosage data when a Bucky-Potter grid is used is expressed as a function g(t), dosage data indicating a shock noise is expressed as n(t), and dosage data indicating an electromagnetic wave noise due to a peripheral device is expressed as m(t). Further, FIG. 5 is a diagram illustrating the relationship between the grid Gm and the radiation detecting pixel 100B.

According to the analysis of the present inventors, as shown in FIG. 4, the dosage data f(t) in imaging when a stationary grid is used or when a grid is not used has a feature of increasing according to startup of the radiation source 22A from a time t0 when irradiation with radiation rays X starts, and maintaining, if the radiation source 22A enters a state where stable irradiation can be performed, an approximately uniform value after electric charges accumulated in the pixel 100B reach a predetermined value. Further, the dosage data n(t) indicating a shock noise generated in the pixel 100B when a shock is applied to the radiation detector 26 has a feature of showing a large peak immediately after the shock, and then, periodically repeating a positive peak and a negative peak along the time axis with its amplitude being gradually reduced. Further, it may be considered that an electromagnetic wave noise from a peripheral device is detected by the radiation detector 26. The dosage data m(t) indicating the electromagnetic wave noise has a feature of showing an approximately feeble and uniform amplitude and periodically repeating a positive peak and a negative peak along the time axis.

Figure 5:
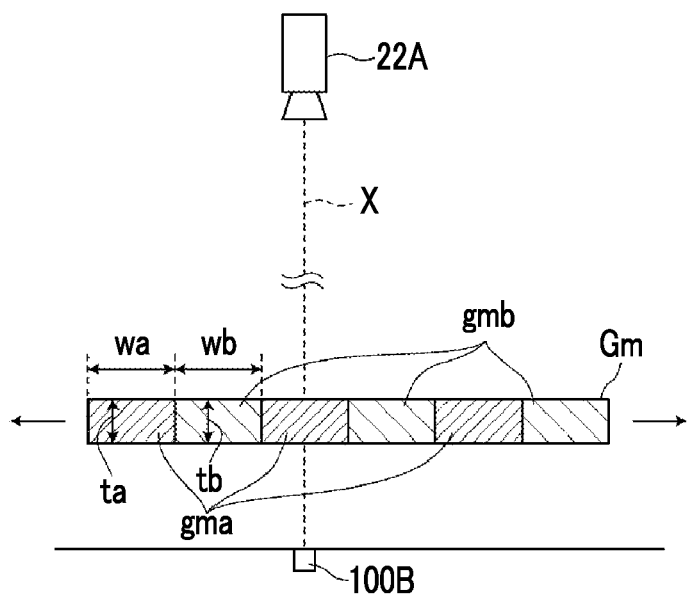
FIG. 5 is a diagram illustrating a principle of the invention.

Here, according to findings of the present inventors during the dosage data analysis, the grid Gm used for radiography has a structure where plural radiation absorbing bodies gma and plural radiation transmitting bodies gmb are alternately adjacently disposed as shown in FIG. 5, and when the grid Gm is rocked to perform radiography, the radiation absorbing bodies gma and the radiation transmitting bodies gmb alternately pass through a space between the pixel 100B and the radiation source 22A. Further, according to the findings, when the grid Gm is rocked to perform radiography, a feature (first feature) indicating a dosage variation as the plural radiation absorbing bodies gma and the radiation transmitting bodies gmb positioned between the adjacent radiation absorbing bodies gma pass through the space between the position of the pixel 100B (specific position) and the radiation source 22A appears in dosage data monitored by the radiation detecting pixel 100B. According to necessary conditions, materials, widths, and thicknesses of the radiation absorbing body gma having a first radiation absorptivity with respect to the grid Gm and the radiation transmitting body gmb having a second radiation absorptivity smaller than the first radiation absorptivity are selected.

This configuration will be specifically described with reference to FIG. 5. Between time points t3 and t5 when the radiation rays X pass through the radiation transmitting bodies gmb according to movement of the grid Gm in an arrow direction in FIG. 5, a radiation dosage depending on absorption of the radiation rays in the radiation transmitting bodies gmb having a thickness tb in an irradiation direction reaches the pixel 100B, between time points t5 and t7 when the radiation rays X pass through the radiation absorbing bodies gma, a radiation dosage depending on absorption of the radiation rays in the radiation absorbing bodies gma having a thickness to in the irradiation direction reaches the pixel 100B, between time points t7 and t9 when the radiation rays X pass through the radiation transmitting bodies gmb, a radiation dosage depending on absorption of the radiation rays in the radiation transmitting bodies gmb having the thickness tb in the irradiation direction reaches the pixel 100B, and between time points t9 and t11 when the radiation rays X pass through the radiation absorbing bodies gma, a radiation dosage depending on absorption of the radiation rays in the radiation absorbing bodies gma having the thickness to in the irradiation direction reaches the pixel 100B. In this way, as the radiation absorbing bodies gma and the radiation transmitting bodies gmb alternately repeatedly transmit the radiation rays, the dosage data in the pixel 100B shows a variation of alternate movement between a dosage value corresponding to the radiation absorbing bodies gma and a dosage value corresponding to the radiation transmitting bodies gmb. According to the invention, the above-described first feature is used. That is, when the dosage data has the first feature, it is determined that a radiographic image corresponding to the dosage data is a rocking grid use image captured by rocking a rocking grid.

The first feature may be specified by an arbitrary method. For example, the first feature may be replaced with a feature 1A or 1B as follows.

(Feature 1A) The dosage data g(t) has approximately sine wave shapes having a uniform amplitude which are adjacent.

When the grid Gm has a configuration in which each radiation absorbing body gma has approximately the same width wa in the movement direction (arrow direction in FIG. 5) and each radiation transmitting body gmb has approximately the same width wb in the movement direction (arrow direction in FIG. 5), due to rocking of the Bucky-Potter grid, adjacent predetermined waveforms having a uniform amplitude in a positive direction and a uniform amplitude in a negative direction are detected in the radiation detecting pixel 100B. Further, each predetermined waveform becomes an approximately sine wave shape since a time lag of electric charges due to a response speed of the pixel 100B occurs with respect to switching of an arrival radiation dosage associated with the rocking of the Bucky-Potter grid. Further, as long as the adjacent sine wave shapes have approximately the same amplitude in the positive direction and have approximately the same amplitude in the negative direction, the amplitude in the positive direction and the amplitude in the negative direction may be different from each other, or may be the same.

In the approximately sine wave shape of one cycle in the dosage data g(t), as the radiation absorption of each radiation transmitting body gmb is reduced, the amplitude in the positive direction (a difference between Vmax and a value (g(t5) in the example shown in FIG. 4) corresponding to the center of the amplitude of the dosage data g(t)) becomes large, and as the radiation absorption of each radiation absorbing body gma is reduced, the amplitude in the negative direction (a difference between Vmin and a value corresponding to the center of the amplitude of the dosage data g(t)) becomes small. Further, at a cycle C1 of the approximately sine wave shape, a period between two inflection points adjacent in the time axis direction (points corresponding to the center of the amplitude of the dosage data g(t)) (for example, a period between the time point t2 and the time point t5 or a period between the time point t5 and the time point t7 in FIG. 4) is determined according to the width wa of the radiation absorbing body gma (or the width wb of the radiation transmitting body gmb) and the speed of the grid Gm in the movement direction. Accordingly, if the width wa of the radiation absorbing body gma, the width wb of the radiation transmitting body gmb, and the speed of the grid Gm in the movement direction are already known, the cycle C1 of the approximately sine wave and the position of the center of the amplitude in the time axis direction can be specified. Further, if the radiation absorption of the radiation absorbing body gma and the thickness thereof in the irradiation direction, and the radiation absorption of the radiation transmitting body gmb and the thickness thereof in the irradiation direction are already known, the amplitude of the sine wave shape in the positive direction and the amplitude thereof in the negative direction can be specified. As a result, it is possible to specify the approximately sine wave shape generated by the grid Gm.

The determining section 43 may employ an arbitrary method for determining the presence or absence of the rocking of the grid Gm by the feature 1A. When the determining section 43 determines the presence or absence of the rocking of the grid Gm by the feature 1A, it is possible to accurately determine a rocking grid use image using dosage data.

For example, the determining section 43 may calculate an approximate curve fitted from plural dosage values of dosage data, may compare the calculated approximate curve with adjacent sine waves having a uniform amplitude, and may determine whether the calculated curve has the adjacent sine wave shapes having the uniform amplitude, to thereby determine the feature 1A. For example, the amplitude or cycle of a sample of the adjacent sine waves having the uniform amplitude used for the comparison may be specified from information on the width wa of the radiation absorbing body gma, the width wb of the radiation transmitting body gmb, the speed of the grid Gm in the movement direction, and the like which are expected to be used. In this case, it is possible to more accurately determine the rocking grid use image. When there are plural grids Gm for rocking imaging which are expected to be used, a sample of a sine wave corresponding to each grid Gm may be prepared, and each sample may be compared with the approximate curve to calculate the feature 1A.

(Feature 1B) As the amount of electric charges accommodated in the pixel 100B is changed according to a variation of the radiation dosage, the dosage data g(t) alternately has a positive maximum value Vmax due to the passage of the radiation transmitting body and a minimum value Vmin which is zero or greater due to the passage of the radiation absorbing body at a uniform interval.

The determining section 43 may employ an arbitrary method for determining a rocking grid use image by the above-mentioned feature 1B. When the determining section 43 determines the rocking grid use image by the feature 1B, it is possible to preferably determine the rocking grid use image by a relatively simple method using the dosage data. For example, the determining section 43 may calculate an approximate curve fitted from plural dosage values of the dosage data, and may detect the positive maximum value Vmax due to the passage of the radiation transmitting body and the minimum value Vmin which is zero or greater due to the passage of the radiation absorbing body in a time-series manner, to thereby determine whether the maximum value Vmax and the minimum value Vmin are alternately repeated. Further, when the presence or absence of the rocking of the grid Gm is determined by the feature 1B, it is possible to determine the rocking of the grid separately from a shock noise and an electromagnetic noise in the dosage data.

In the grid Gm according to this embodiment, the thickness tb of each radiation transmitting body gmb in the radiation direction and the thickness to of each radiation absorbing body gma in the irradiation direction of radiation rays match each other, and the width wb of each radiation transmitting body gmb in the movement direction and the width wa of each radiation absorbing body gma in the movement direction match each other.

Returning to FIG. 3, the grid stripe detector 45 detects the presence or absence of a grid stripe which is a stripe shape due to a grid used in imaging, in a radiographic image. Specifically, the grid stripe detector 45 frequency-analyzes the radiographic image to obtain a frequency spectrum, and determines whether a peak is present in a certain frequency component in the frequency spectrum. Here, since a cycle stripe due to the cycle of the grid and a moiré pattern generated due to the cycle stripe by sampling of the radiographic image are included in the radiographic image acquired by imaging using the grid, a peak is present in a frequency component corresponding to the grid cycle and the moiré pattern, in the frequency spectrum. Accordingly, by determining whether the peak is present or not in the acquired frequency spectrum, the grid stripe detector 45 detects the presence or absence of the grid stripe in the radiographic image.

Further, the grid stripe detector 45 adds determination information indicating whether it is determined that the radiographic image is the stationary grid use image as additional information with respect to the radiographic image. After the process of determining whether the radiographic image is the stationary grid use image is executed, the respective sections of the determining section 43, the grid stripe detector 45, the grid stripe suppressing section 46, the scattered ray suppressing section 47, the display controller 49, and the like determine a necessary process and an unnecessary process for the stationary grid use image, with reference to the additional information of the radiographic image as necessary.

The grid stripe suppressing section 46 performs a grid stripe suppression process of suppressing a frequency component corresponding to an image (grid stripe) indicating a stationary imaging grid included in a stationary grid use image from the stationary grid use image. As the grid stripe suppression process, a filtering process using a filter that reduces the frequency component corresponding to the grid stripe may be used, for example.

Figure 6:
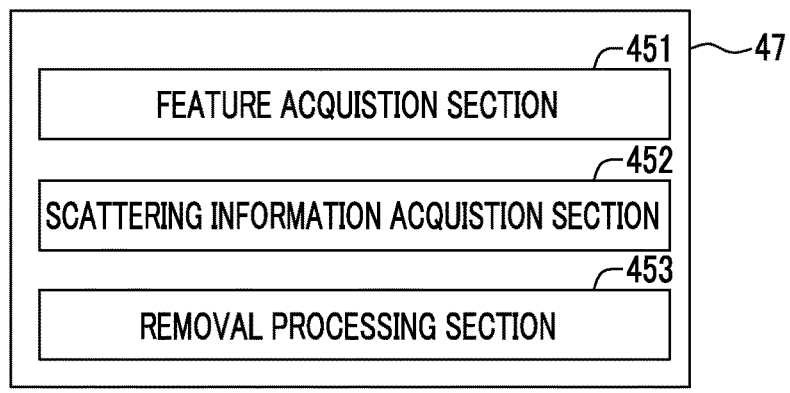
FIG. 6 is a schematic block diagram illustrating a configuration of a scattered ray suppressing section.

The scattered ray suppressing section 47 performs a scattered ray component suppression process of generating a scattered ray image indicating a scattered ray component in each position of a grid non-use image from the grid non-use image, and subtracting the scattered ray image from the grid non-use image. FIG. 6 is a schematic block diagram illustrating a configuration of the scattered ray suppressing section 47. As shown in FIG. 6, the scattered ray suppressing section 47 includes a feature acquisition section 451 that acquires a virtual grid feature which is a feature of a virtual grid expected to be used for removing scattered rays when capturing a radiographic image, a scatter information acquisition section 452 that acquires scattered component information indicating scattered components of radiation rays included in a radiographic image, and a removal processing section 453 that performs a scattered ray suppression process for a radiographic image acquired by the radiation detector 26 based on the virtual grid feature acquired by the feature acquisition section 451 and the scattered component information acquired by the scatter information acquisition section 452.

The feature acquisition section 451 receives an operation input from an operator by the operation input detector 52, and acquires a virtual grid feature according to the received operation input. In this embodiment, the virtual grid feature includes a scattered ray transmissivity Ts for the virtual grid, and a transmissivity Tp of primary rays (primary ray transmissivity) that pass through a photographic subject which is the examinee 30 to be directly applied to the radiation detector 26. The scattered ray transmissivity Ts and the primary ray transmissivity Tp have a value of 0 to 1.

The feature acquisition section 451 may directly receive inputs of the values of the scattered ray transmissivity Ts and the primary ray transmissivity Tp to obtain the virtual grid feature, but in this embodiment, the feature acquisition section 451 receives at least one designation of grid information indicating the type of the grid, information (photographic subject information) on a photographic subject, and an imaging condition when capturing a radiographic image to obtain the virtual grid feature, that is, the scattered ray transmissivity Ts and the primary ray transmissivity Tp.

Here, the grid information includes at least one piece of information among a variety of information for specifying the type of the grid, such as a grid ratio, a grid density, whether the grid is a convergence type or a parallel type, a focusing distance in the case of the convergence type, and an inter-space material (aluminum, fiber, Bakelite or the like). The scattered ray transmissivity Ts and the primary ray transmissivity Tp are changed according to the type of the grid. Thus, a table in which at least one of a variety of grid information and the virtual grid feature are associated with each other is stored in the storage section 44, with respect to the grid information.

The photographic subject information includes the type of photographic subject such as a chest portion, an abdominal portion, or a head portion. Here, when capturing a radiographic image, the type of a grid to be used is generally determined according to an imaging portion, and the scattered ray transmissivity Ts and the primary ray transmissivity Tp are changed according to the type of the grid. Thus, a table in which the variety of photographic subject information and the virtual grid feature are associated with each other is stored in the storage section 44, with respect to the photographic subject information.

The imaging condition includes at least one of an imaging distance (SID: Source to Image receptor Distance) in imaging, an imaging dosage, a tube voltage, a target of a radiation source and materials of a filter, and the type of a radiation detector to be used in imaging. Here, when capturing a radiographic image, the type of the grid to be used is generally determined according to the imaging condition, and the scattered ray transmissivity Ts and the primary ray transmissivity Tp are changed according to the type of the grid. Thus, a table in which the various imaging conditions are associated with the virtual grid feature is stored in the storage section 44, with respect to the imaging condition. In many cases, the various imaging conditions are determined according to facilities where the radiation imaging system is installed. Thus, when an imaging condition in actual imaging is not clear, the imaging conditions according to the facilities may be used.

The feature acquisition section 451 receives an operation input from an operator by the operation input detector 52 with reference to the tables stored in the storage section 44, and acquires the virtual grid feature based on at least one of the grid information, the photographic subject information, and the imaging condition acquired according to the received operation input. The feature acquisition section 451 may directly receive inputs of the grid information, the photographic subject information, and the imaging conditions through an input section 9. Alternatively, a list of a variety of grid information, a variety of photographic subject information, and various imaging conditions may be displayed on the display 50, and at least one selection of grid information, photographic subject information, and an imaging condition from the list may be received to perform input of the grid information, the photographic subject information, and the imaging condition. Further, the imaging condition may be acquired from the radiation controller 62.

When the imaging condition is an imaging dosage, an acrylic model of which the thickness is already known may be imaged together with a photographic subject, and the imaging dosage may be acquired based on the concentration of a portion of the acrylic model in the acquired radiographic image. In this case, a table in which the concentration of the acrylic model and the imaging dosage are associated with each other may be stored in the storage section 44, and the imaging dosage may be acquired based on the concentration of the acrylic model with reference to the table. Further, when a passing-through region acquired by directly irradiating the radiation detector 26 with radiation rays is included in a radiographic image, the image dosage may be acquired based on the concentration of the passing-through region. In this case, a table in which the concentration of the passing-through region and the imaging dosage are associated with each other may be stored in the storage section 44, and the imaging dosage may be acquired based on the concentration of the passing-through region with reference to the table. In addition, the imaging dosage may be measured using a dosage meter, and the measured imaging dosage may be used as the imaging condition.

Further, in this embodiment, the scattered ray suppression process is performed by frequency decomposition of a radiographic image as described later. In this embodiment, the virtual grid feature is acquired with respect to each of plural frequency bands of the radiographic image acquired by the frequency decomposition. Thus, the virtual grid feature in the table is associated with each of the plural frequency bands.

Further, a table in which all of the grid information, the photographic subject information and the imaging conditions are associated with the virtual grid feature may be stored in the storage section 44, and the virtual grid feature may be acquired based on all of the grid information, the photographic subject information, and the imaging conditions. In this case, the table is formed as at least a four-dimensional table in which a variety of grid information, a variety of photographic subject information and various imaging conditions, and the virtual grid feature are associated with each other.

An exposure magnifying factor which is an increasing rate of irradiation dosage that increases as the grid is used, a contrast improvement coefficient which is the ratio of contrast when the grid is used to contrast when the grid is not used, and a selectivity which is the ratio of a primary X-ray transmissivity to a scattered X-ray transmissivity are feature values indicating features of the grid. The scattered ray transmissivity Ts and the primary ray transmissivity Tp may be calculated from these feature values. Thus, by receiving at least one designation of the exposure magnifying factor, the contrast improvement coefficient, and the selectivity in the feature acquisition section 451, the virtual grid feature, that is, the scattered ray transmissivity Ts and the primary ray transmissivity Tp may be calculated and acquired.

Further, in this embodiment, the scattered ray suppressing section 47 performs the scattered ray suppression process based on scattered component information in addition to the virtual grid feature. Thus, the scatter information acquisition section 452 acquires scattered component information. In this embodiment, for example, if the photographic subject is a chest portion, the scattered component information shows a scattered ray content distribution in a radiographic image, in which there is a large amount of scattered rays in a central portion of the radiographic image where a mediastinal space is present, and there is a small amount of scattered rays in a peripheral portion where a lung field is present.

The scatter information acquisition section 452 analyzes a radiographic image acquired by imaging to obtain scattered component information, that is, a scattered ray content distribution. The analysis of the radiographic image is performed based on irradiation field information, photographic subject information, and an imaging condition when capturing the radiographic image.

The irradiation field information refers to information indicating an irradiation field distribution relating to the position and size of an irradiation field included in a radiographic image when imaging is performed using an irradiation field diaphragm. The photographic subject information refers to information relating to a position of a photographic subject on a radiographic image, a composition distribution of the photographic subject, the size of the photographic subject, the thickness of the photographic subject, and the like, in addition to the type of the photographic subject such as the chest portion, the abdominal portion or the head portion. The imaging condition refers to information relating to an irradiation dosage in imaging (tube current×irradiation time), a tube voltage, an imaging distance (the sum of a distance from a radiation source to a photographic subject and a distance from the photographic subject to a radiation detector), an air gap (the distance from the photographic subject to the radiation detector), a feature of the radiation detector, and the like. The irradiation field information, the photographic subject information, and the imaging condition are factors for determining the distribution of the scattered rays included in the radiographic image. For example, the amount of the scattered rays is determined by the size of the irradiation field. As the thickness of the photographic subject becomes larger, the amount of the scattered rays is increased, and if air is present between the photographic subject and the radiation detector, the amount of the scattered rays is decreased. Accordingly, by using the above-mentioned information, it is possible to obtain an accurate scattered ray content distribution.

The scatter information acquisition section 452 calculates a primary ray image and a scattered ray image according to the following Expressions (1) and (2) from a thickness distribution $T(x, y)$ of a photographic subject in a radiographic image acquired by imaging, and calculates a scattered ray content distribution $S(x, y)$ according to Expression (3) from the calculated primary image and scattered ray image. The scattered ray content distribution S(x, y) has values of 0 to 1.

$$Icp(x,y)=Io(x,y)\times \exp(-\mu \times T(x,y)) \quad (1)$$

$$Ics(x,y)=Io(x,y)*S\sigma(T(x,y)) \quad (2)$$

$$S(x,y)=Ics(x,y)/(Ics(x,y)+Icp(x,y)) \quad (3)$$

Here, (x, y) represents coordinates of a pixel position in a radiographic image, Icp(x, y) represents a primary ray image at the pixel position (x, y), Ics(x, y) represents a scattered ray image at the pixel position (x, y), Io(x, y) represents an incident dosage to a surface of a photographic subject at the pixel position (x, y), μ represents a linear attenuation coefficient, and Sσ(T(x, y) represents a convolution kernel indicating a feature of scattering according to the thickness of the photographic subject at the pixel position (x, y). Expression (1) is an expression based on a known index attenuation rule, Expression (2) is an expression based on a technique disclosed in "J M Boon et al, An analytical model of the scattered radiation distribution in diagnostic radiolog, Med, Phys. 15(5), September/October 1988" (Reference Document 1). No matter what value the incident dosage Io(x, y) to the front surface of the photographic subject is defined as, the incident dosage Io(x, y) is canceled due to division when calculating S(x, y), and thus, the incident dosage Io(x, y) may be set to an arbitrary value, for example, may be set to 1.

Further, the thickness distribution T(x, y) of the photographic subject may be calculated by assuming that a luminance distribution in a radiographic image approximately matches a thickness distribution of the photographic subject, and converting a pixel value of the radiographic image into a thickness by a value of the linear attenuation coefficient. Instead, the thickness of the photographic subject may be measured by using a sensor or the like, or may be approximated by a model such as a cube or an elliptic cylinder.

Here, * in Expression (2) represents an operator indicating a convolution operation. A characteristic of the kernel is changed not only according to the thickness of the photographic subject, but is also changed according to an irradiation field distribution, a composition distribution of the photographic subject, an irradiation dosage in imaging, a tube voltage, an imaging distance, an air gap, and characteristics of a radiation detector, and the like. According to the technique disclosed in Reference Document 1, the scattered rays may be approximated by a convolution of a point spread function (Sσ(T(x, y)) in Expression (2)) with respect to the primary rays. Sσ(T(x, y)) may be experimentally calculated according to irradiation field information, photographic subject information, an imaging condition, and the like.

In this embodiment, Sσ(T(x, y)) may be calculated based on the irradiation field information in imaging, the photographic subject information, and the imaging condition, but a table in which a variety of irradiation field information, a variety of photographic subject information, and various imaging conditions are associated with Sσ(T(x, y)) may be stored in the storage section 44, and Sσ(T(x, y)) may be calculated based on the irradiation field information in imaging, the photographic subject information, and the imaging conditions with reference to the table. Sσ(T(x, y)) may be approximated by T(x, y).

The removal processing section 453 performs a scattered ray suppression process by reducing a frequency component in a frequency band which can be considered as scattered rays in a radiographic image based on a virtual grid feature and scattered component information. Thus, the removal processing section 453 frequency-decomposes the radiographic image to obtain a frequency component for each of plural frequency bands, performs a process of reducing a gain of at least one frequency component, and composes the processed frequency component and other frequency components to obtain a radiographic image which is subjected to the scattered ray suppression process. As a frequency-decomposition method, a method for performing multiple resolution conversion with respect to a radiographic image may be used. Further, a known arbitrary method such as wavelet transform or Fourier transform may be used.

The removal processing section 453 calculates a conversion coefficient R(x, y) for converting a frequency component from the scattered ray transmissivity Ts and the primary ray transmissivity Tp which form the virtual grid feature, and the scattered ray content distribution S(x, y) using the following Expression (4).

$$R(x,y)=S(x,y)\times Ts+(1-S(x,y))\times Tp \quad (4)$$

Since the scattered ray transmissivity Ts and the primary ray transmissivity Tp, and the scattered ray content distribution S(x, y) have values of 0 to 1, the conversion coefficient R(x, y) also becomes a value of 0 to 1. The removal processing section 453 calculates the conversion coefficient R(x, y) for each of the plural frequency bands.

In the following description, a pixel value of a radiographic image is represented as I(x, y), a frequency component image acquired by frequency decomposition is represented as I(x, y, r), a frequency composition is represented as I(x, y)=ΣrI(x, y, r), a conversion coefficient for each frequency band is represented as R(x, y, r), and a scattered ray transmissivity and a primary ray transmissivity for each frequency band are represented as Ts(r) and Tp(r). r represents a layer of a frequency band. As r becomes larger, it means a lower frequency. Accordingly, I(x, y, r) represents a frequency component image in a certain frequency band. The scattered ray content distribution S(x, y) may employ a value calculated with respect to a radiographic image, and may be acquired with respect to each of the frequency bands, similar to the scattered ray transmissivity Ts and the primary ray transmissivity Tp.

In this embodiment, the conversion coefficient R(x, y, r) is calculated for each frequency band, the frequency component image I(x, y, r) is multiplied by the conversion coefficient R(x, y, r) of a corresponding frequency band to convert a pixel value of the frequency component image I(x, y, r), and the frequency component images I(x, y, r) multiplied by the conversion coefficients R(x, y, r) (that is, I(x, y, r)×R(x, y, r)) are frequency-composed to obtain a processed radiographic image I'(x, y). Accordingly, the process performed in the removal processing section 453 is expressed by the following Expression (5). Since the conversion coefficient R(x, y, r) has a value of 0 to 1, as the frequency component (x, y, r) is multiplied by the conversion coefficient R(x, y, r) of the corresponding frequency band, a pixel value at the pixel position (x, y) of the frequency component, that is, a gain is reduced.

$$I'(x, y) = \Sigma r\{I(x, y, r)\times R(x, y, r)\} \quad (5)$$
$$= \Sigma r\{I(x, y, r)\times (S(x, y)\times Ts(r) + (1 - S(x, y))\times Tp(r))\}$$

Here, in this embodiment, a radiographic image is frequency-decomposed into six frequency bands, and the scattered ray transmissivity Ts and the primary ray transmissivity Tp are acquired with respect to six frequency bands. In this case, the scattered ray transmissivity Ts and the primary ray transmissivity Tp become values as shown in the following Expression (6). In Expression (6), a value of a low frequency band is written on a right side.

$$Ts=\{0.7, 0.7, 0.7, 0.7, 0.3, 0.2\}$$

$$Tp=\{0.7, 0.7, 0.7, 0.7, 0.7, 0.7\} \quad (6)$$

As shown in Expression (6), the scattered ray transmissivity Ts and the primary ray transmissivity Tp are the same values at high frequency bands (r=1 to 4), but the scattered ray transmissivity Ts becomes a lower value at low frequency bands (r=5 to 6). This is because a grid has a high removal rate but has a small frequency dependency of a removal rate with respect to primary rays in a low frequency band where a frequency component of scattered rays is dominant.

Figure 7:
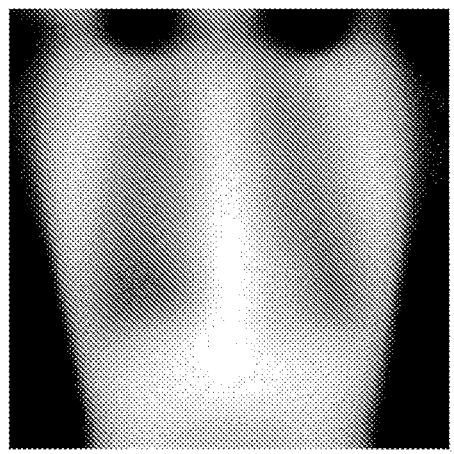
FIG. 7 is a diagram illustrating a scattered ray content distribution in a radiographic image of a chest portion.
Figure 8:
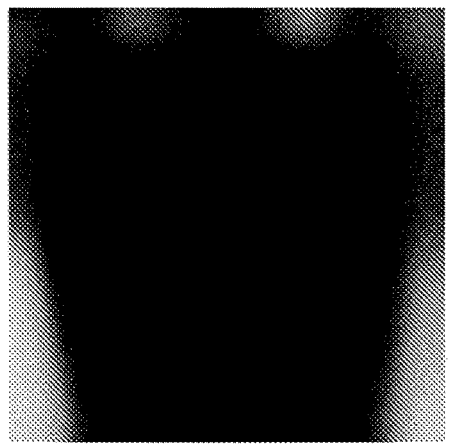
FIG. 8 is a diagram illustrating a conversion factor calculated in a case where the scattered ray content distribution is shown in FIG. 7.

FIG. 7 is a diagram illustrating a scattered ray content distribution S(x, y) in a radiographic image of a chest portion. In FIG. 7, as the scattered ray content distribution S(x, y) becomes higher, a luminance at each pixel position becomes higher. It can be understood from FIG. 7 that, in the image of the chest portion, the content of scattered rays is high in a mediastinal portion and a peripheral portion of a lung field. In the case of such a scattered ray content distribution S(x, y), a conversion coefficient calculated based on Expressions (4) and (6) is shown in FIG. 8. In FIG. 8, as luminance becomes lower, a value of the conversion coefficient becomes smaller, and a pixel value is greatly reduced. When comparing FIG. 7 with FIG. 8, it can be understood that the value of the conversion coefficient becomes smaller in the mediastinal portion and the peripheral portion of the lung field where the content of the scattered rays is high. Accordingly, in a processed radiographic image acquired by performing the process shown in Expression (5) using the calculated conversion coefficient, the scattered ray component is removed according to the type of a grid to be used.

The removal processing section 453 may remove scattered rays of a radiographic image as follows. First, when the frequency composition is represented as I(x, y)=ΣrI(x, y, r) as described above, the removal processing section 453 decomposes the frequency component image I(x, y, r) into a scattering component Ics(x, y, r) and a primary ray component Icp(x, y, r) using the scattered ray content distribution S(x, y) using the following Expression (7).

$$Ics(x,y,r)=S(x,y)\times I(x,y,r)$$

$$Icp(x,y,r)=(1-S(x,y))\times I(x,y,r) \quad (7)$$

Further, the removal processing section 453 respectively applies a scattered ray transmissivity Ts(r) and a primary ray transmissivity Tp(r) which form a virtual grid feature to the scattering component Ics(x, y, r) and the primary ray component Icp(x, y, r) for image conversion, and calculates a converted scattering component Ics'(x, y, r) and a converted primary ray component Icp'(x, y, r) using the following Expression (8).

$$Ics'(x,y,r)=Ics(x,y,r)\times Ts(r)=S(x,y)\times I(x,y,r)\times Ts(r)$$

$$Icp'(x,y,r)=Icp(x,y,r)\times Tp(r)=(1-S(x,y))\times I(x,y,r)\times Tp(r) \quad (8)$$

Further, the removal processing section 453 frequency-composes the Ics'(x, y, r) and the primary ray component Icp'(x, y, r) to calculate a processed radiographic image I(x, y)', using the following Expression (9).

$$I'(x, y) = \Sigma r\{Ics'(x, y, r) + Icp'(x, y, r)\} \quad (9)$$
$$= \Sigma r\{S(x, y) \times I(x, y, r) \times Ts(r) +$$
$$(1 - S(x, y)) \times I(x, y, r) \times Tp(r)\}$$
$$= \Sigma r\{I(x, y, r) \times (S(x, y) \times Ts(r) + (1 - S(x, y)) \times Tp(r))\}$$

It is preferable that the scattered ray suppressing section 47 estimates a thickness distribution of a photographic subject (examinee 30) as necessary, and performs a scattered ray suppression process so as to reduce scattered rays at a position where a body thickness of the photographic subject is large according to the estimated thickness distribution of the photographic subject. As a body thickness distribution estimation method, an arbitrary method may be used. For example, a method disclosed in JP1990-244881A (JP-H02-244881A) may be used. Further, when employing a method disclosed in JP2013-229941 which is an application of the present applicant, a body thickness distribution estimated with high accuracy may be applied to the scattered ray suppression process, to thereby make it possible to appropriately perform the scattered ray suppression process depending on the body thickness distribution of the photographic subject.

Returning to FIG. 3, the image processing section 48 performs necessary image processing such as a noise removal process of removing noise, grayscale processing and frequency processing with respect to a stationary grid use image which is subjected to the grid stripe suppression process, a grid non-use image which is subjected to the scattered ray suppression process, and a rocking grid use image which is not subjected to the grid stripe suppression process or the scattered ray suppression process, to thereby obtain a processed radiographic image. The image processing section 48 stores the processed image which is subjected to the necessary image processing in the storage unit 17.

Further, the image processing section 48 prepares, with respect to three types of images of the rocking grid use image, the stationary grid use image, and the grid non-use image, a setting table in which image processing parameters for necessary image processing of the respective types of images are set in advance so that image qualities of the three types of processed images match each other. The image processing section 48 performs necessary image processing based on an image processing parameter for the rocking grid use image with respect to the rocking grid use image, performs necessary image processing based on an image processing parameter for the stationary grid use image with respect to the stationary grid use image, and performs necessary image processing based on an image processing parameter for the grid non-use image with respect to the grid non-use image, according to the setting table.

The display controller 49 displays the processed radiographic image on the display 50. The stationary grid use image which is subjected to the grid stripe suppression process, the grid non-use image which is subjected to the scattered ray suppression process, and the rocking grid use image which is not subjected to the grid stripe suppression process or the scattered ray suppression process are subjected to the image processing to be displayed on the display 50. In the following description, the radiographic image which is subjected to the image processing is represented as a radiographic image G0, the radiographic image which is subjected to the grid stripe suppression process and the image processing is represented as a radiographic image G1, and the radiographic image which is subjected to the scattered ray suppression process and the image processing is represented as a radiographic image G2.

Figure 9:
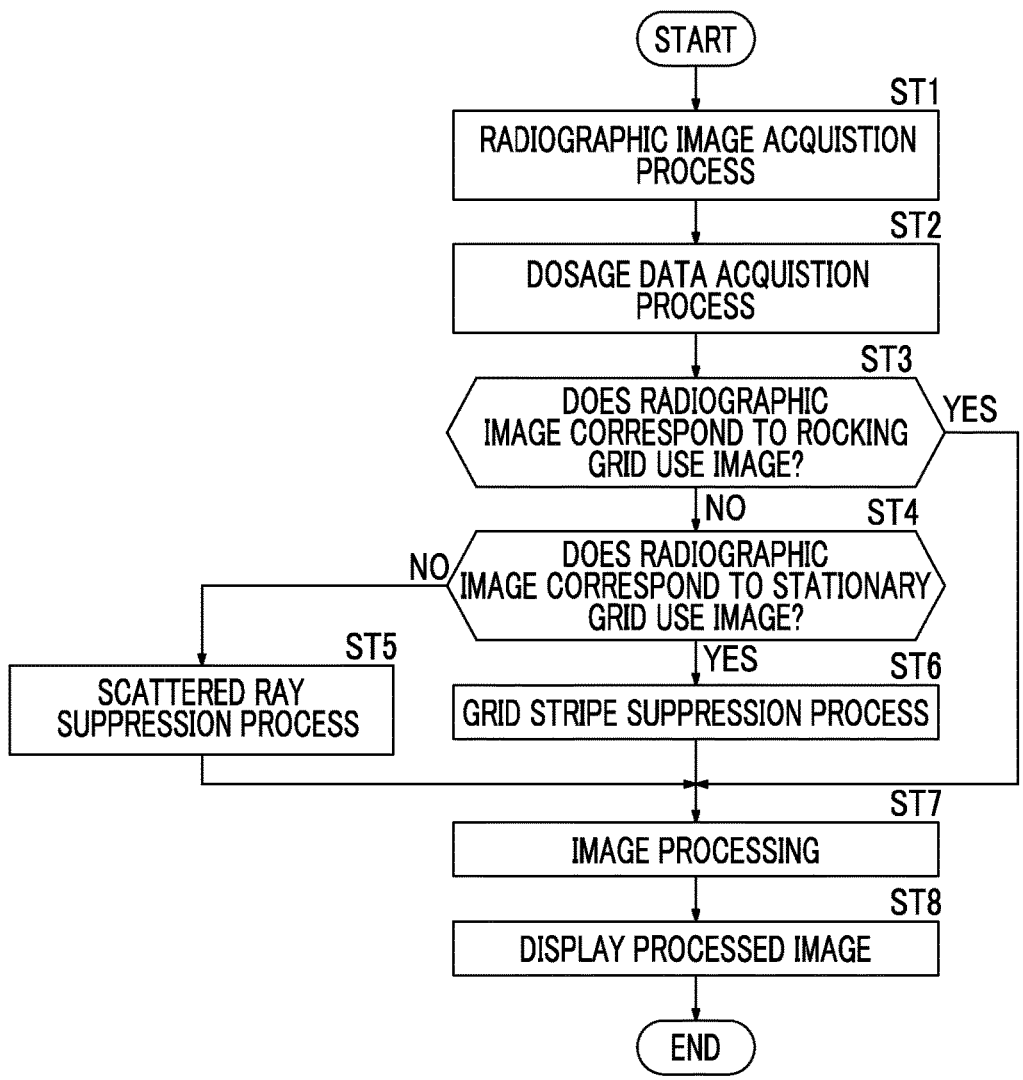
FIG. 9 is a flowchart illustrating a process performed in the first embodiment.

Next, a process performed in a first embodiment will be described. FIG. 9 is a flowchart illustrating the process performed in the first embodiment. The image acquisition section 41 acquires a radiographic image corresponding to acquired dosage data (step ST1). Then, the dosage data acquisition section 42 acquires the dosage data (step ST2), and then, the determining section 43 determines the presence or absence of the first feature in the dosage data based on the dosage data, and determines that a radiographic image corresponding to the dosage data having the first feature corresponds to a rocking grid use image (step ST3, Yes). When it is determined that the radiographic image corresponds to the rocking grid use image, the determining section 43 sets an image processing parameter for the rocking grid use image with respect to the rocking grid use image and performs necessary image processing to generate a radiographic image G0 which is subjected to the image processing (step ST7). Further, the display controller 49 displays the radiographic image G0 on the display 50 (step ST8).

Further, when it is determined by the determining section 43 that the dosage data does not have the first feature, that is, when it is determined that the radiographic image does not correspond to the rocking grid use image (step ST3, No), the grid stripe detector 45 detects the presence or absence of a grid stripe of the radiographic image. If the grid stripe is detected by the grid stripe detector 45, the determining section 43 determines that the radiographic image in which the grid stripe is detected is a stationary grid use image (step ST4, Yes). Then, the grid stripe suppressing section 46 performs the grid stripe suppression process with respect to the stationary grid use image (step ST6), and the image processing section 48 sets an image processing parameter for the stationary grid use image with respect to the stationary grid use image which is subjected to the grid stripe suppression process and performs necessary image processing to generate a radiographic image G1 which is subjected to the image processing (step ST7). Further, the display controller 49 displays the radiographic image G1 on the display 50 (step ST8).

In addition, when the grid stripe detector 45 detects the presence or absence of the grid stripe of the radiographic image and the grid stripe is not detected by the grid stripe detector 45, the determining section 43 determines that the radiographic image in which the grid stripe is not detected is a grid non-use image (step ST4, No). Then, the scattered ray suppressing section 47 performs the scattered ray suppression process with respect to the grid non-use image (step ST5), and the image processing section 48 sets an image processing parameter for the grid non-use image with respect to the grid non-use image which is subjected to the scattered ray suppression process and performs the necessary image processing to generate a radiographic image G2 which is subjected to the image processing (step ST7). Further, the display controller 49 displays the radiographic image G2 on the display 50 (step ST8).

An image analysis device terminates the process according to a user's instruction for terminating the display of the processed image. The processed radiographic image is stored in the storage section 44, or is transmitted to a server network-connected to the console 16 to be stored in the storage unit 17.

According to this embodiment (first embodiment), dosage data indicating, in a time-series manner, a dosage of radiation rays exposed to a specific position in an imaging region corresponding to a radiographic image in a specific period including an imaging period of the radiographic image is acquired, it is determined whether the dosage data has a first feature indicating a dosage variation as plural radiation absorbing bodies and radiation transmitting bodies disposed between adjacent radiation absorbing bodies pass through a space between the specific position and a radiation source used for radiography, and it is determined that a radiographic image corresponding to dosage data determined to have the first feature is a rocking grid use image captured by rocking a grid for removing scattered rays. Thus, it is possible to appropriately determine whether the radiographic image is captured by rocking the grid using the dosage data. In addition, it is possible to appropriately apply the determined information to a technique for performing different image processing according to the presence or absence of use of a Bucky-Potter grid, for example.

Further, in this embodiment, since the determining section 43 can determine that a radiographic image corresponding to dosage data determined not to have the first feature is any one of a stationary grid use image captured with the grid for removing scattered rays being stationary and a grid non-use image captured with the grid for removing the scattered rays not being used, it is possible to appropriately determine the presence or absence of the use of the rocking grid.

In addition, in this embodiment, since the determining section 43 can determine whether a radiographic image has a second feature indicating that the radiographic image includes a grid image for stationary imaging, determine that a radiographic image determined to have second feature is a stationary grid use image, and determine that a radiographic image that corresponds to dosage data determined not to have the first feature and is determined not to have the second feature is a grid non-use image, it is possible to appropriately determine a rocking grid use image, a stationary grid use image, and a grid non-use image.

Further, in this embodiment, the grid stripe suppressing section 46 that suppresses a frequency component corresponding to an image (grid stripe) indicating a stationary imaging grid included in a stationary grid use image from the stationary grid use image is provided. Thus, it is possible to prevent the grid stripe suppression process from being mistakenly performed with respect to a grid non-use image and a rocking grid use image which are images without a grid stripe according to a determination result of the type of the grid. As a result, it is possible to generate an image which is properly processed for display.

Further, in this embodiment, the scattered ray suppressing section 47 that performs a scattered ray component suppression process of generating a scattered ray image indicating a scattered ray component in each position of a grid non-use image from the grid non-use image, and subtracting the scattered ray image from the grid non-use image is provided. Thus, according to the determination result of the type of the grid, it is possible to prevent the scattered ray suppression process from being mistakenly performed with respect to the stationary grid use image and the rocking grid use image. As a result, it is possible to generate an image which is properly processed for display.

In this embodiment, the determining section 43 adds determination information indicating whether it is determined that the radiographic image is the rocking grid use image as additional information of the radiographic image to the radiographic image, and determines a necessary process and an unnecessary process for the rocking grid use image, with reference to the additional information of the radiographic image in a subsequent process. Thus, it is possible to easily determine whether the radiographic image is the rocking grid non-use image, and thus, it is possible to provide information suitable for a request for changing the type or the presence or absence of the process according to whether the radiographic image is the rocking grid use image.

Further, since the image processing section 48 executes necessary image processing depending on the type of each image using an image processing parameter suitable for the type of each image, with respect to three types of images of the rocking grid use image, the stationary grid use image, and the grid non-use image, it is possible to cause image qualities of the processed images to match each other, and to provide processed images suitable for comparison and observation of different types of processed images. Such image processing may be suitably applied to a case where different types of processed images are compared and observed, for example, when temporal comparison and observation are performed using previous radiographic images in order to perform diagnosis of a healing state of a disease or a progressing state thereof. Further, since the image processing section 48 executes necessary image processing depending on the type of each image using an image processing parameter suitable for the type of each image with respect to three types of images of the rocking grid use image, the stationary grid use image, and the grid non-use image, it is possible to reduce the burden of an operation input of an operator, and to accurately and efficiently perform the image processing with respect to each image.

Figure 10:
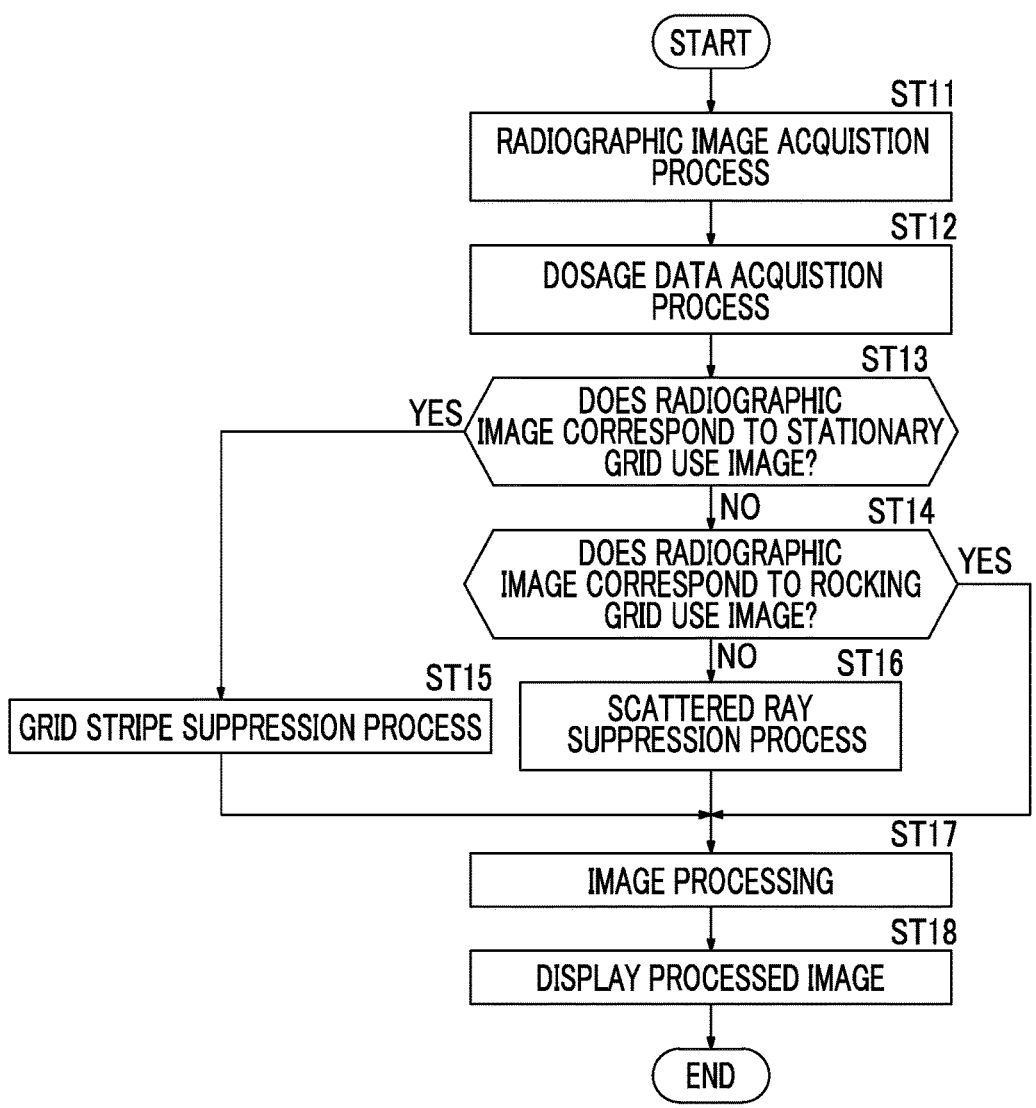
FIG. 10 is a flowchart illustrating a process performed in a second embodiment.

As in the first embodiment, when the determining section 43 is configured to be able to determine the stationary grid use image and the rocking grid use image, any one of a process of determining the stationary grid use image and a process of determining the rocking grid use image may be preferentially performed, or the processes may be performed at the same time. As a second embodiment, an example in which the order of the process of determining the stationary grid use image and the process of determining the rocking grid use image in the determining section 43 is reversed with respect to the first embodiment will be described. FIG. 9 is a flowchart illustrating a process performed in the second embodiment. Since the second embodiment is different from the first embodiment in that the order of the processes is changed in the image analysis device, and components and functions thereof are the same as in the first embodiment, description about the common parts will not be repeated. The flow of processes in the image analysis device in the second embodiment will be described with reference to FIG. 10.

First, the image acquisition section 41 acquires a radiographic image corresponding to acquired dosage data (step ST11). Then, the dosage data acquisition section 42 acquires the dosage data (step ST12), and then, the grid stripe detector 45 detects the presence or absence of a grid stripe of the radiographic image. When the grid stripe is detected by the grid stripe detector 45, the determining section 43 determines that the radiographic image in which the grid stripe is detected corresponds to a stationary grid use image (step ST13, Yes). Then, the grid stripe detector 46 performs a grid stripe suppression process with respect to the stationary grid use image (step ST15), and the image processing section 48 performs necessary image processing with respect to the stationary grid use image which is subjected to the grid stripe suppression process to generate a processed radiographic image G1 (step ST17). Further, the display controller 49 displays the radiographic image G1 on the display 50 (step ST18).

Further, when the grid stripe is not detected from the radiographic image by the grid stripe detector 45, the determining section 43 determines that the radiographic image does not correspond to the stationary grid use image (step ST13, No). In this case, the determining section 43 determines the presence or absence of a first feature of dosage data based on the dosage data, and determines a radiographic image corresponding to dosage data that has the first feature as a rocking grid use image (step ST14, Yes). Then, the image processing section 48 performs necessary image processing with respect to the rocking grid use image to generate a processed radiographic image G0 (step ST17). Further, the display controller 49 displays the radiographic image G0 on the display 50 (step ST18).

In addition, the determining section 43 determines the presence or absence of the first feature of the dosage data based on the dosage data, and determines that the radiographic image corresponding to the dosage data that does not have the first feature does not correspond to the rocking grid use image (step ST14, No). In this case, since the radiographic image is an image that does not correspond to the stationary grid use image and the rocking grid use image, the determining section 43 determines that the radiographic image is a grid non-use image. Then, the scattered ray suppressing section 47 performs a scattered ray suppression process with respect to the grid non-use image (step ST16), and the image processing section 48 performs necessary image processing with respect to the grid non-use image which is subjected to the scattered ray suppression process to generate a radiographic image G2 which is subjected to the image processing (step ST17). Further, the display controller 49 displays the radiographic image G2 on the display 50 (step ST18).

As described in the second embodiment, even when the order of the rocking grid use image determination process and the stationary grid use image determination process is changed, it is possible to obtain the same effects as in the first embodiment. It is preferable that the order of the rocking grid use image determination process and the stationary grid use image determination process is determined according to necessary conditions in each system.

Further, the determining section 43 may use a combination of the process of determining the rocking grid use image according to whether the dosage data has the first feature and the process of determining the rocking grid use image by a different method. As a third embodiment which is a modification of the first embodiment, an example in which, the determining section 43 determines whether rocking grid information indicating that a radiographic image is captured by rocking a rocking imaging grid is included in imaging instruction information indicating an imaging instruction of the radiographic image, determines, when it is determined that the rocking grid information is included in the imaging instruction information, a rocking grid use image based on the rocking grid information in the imaging instruction information, and determines, when it is determined that the rocking grid information is not included in the imaging instruction information, whether dosage data has the first feature, will be described.

Figure 11:
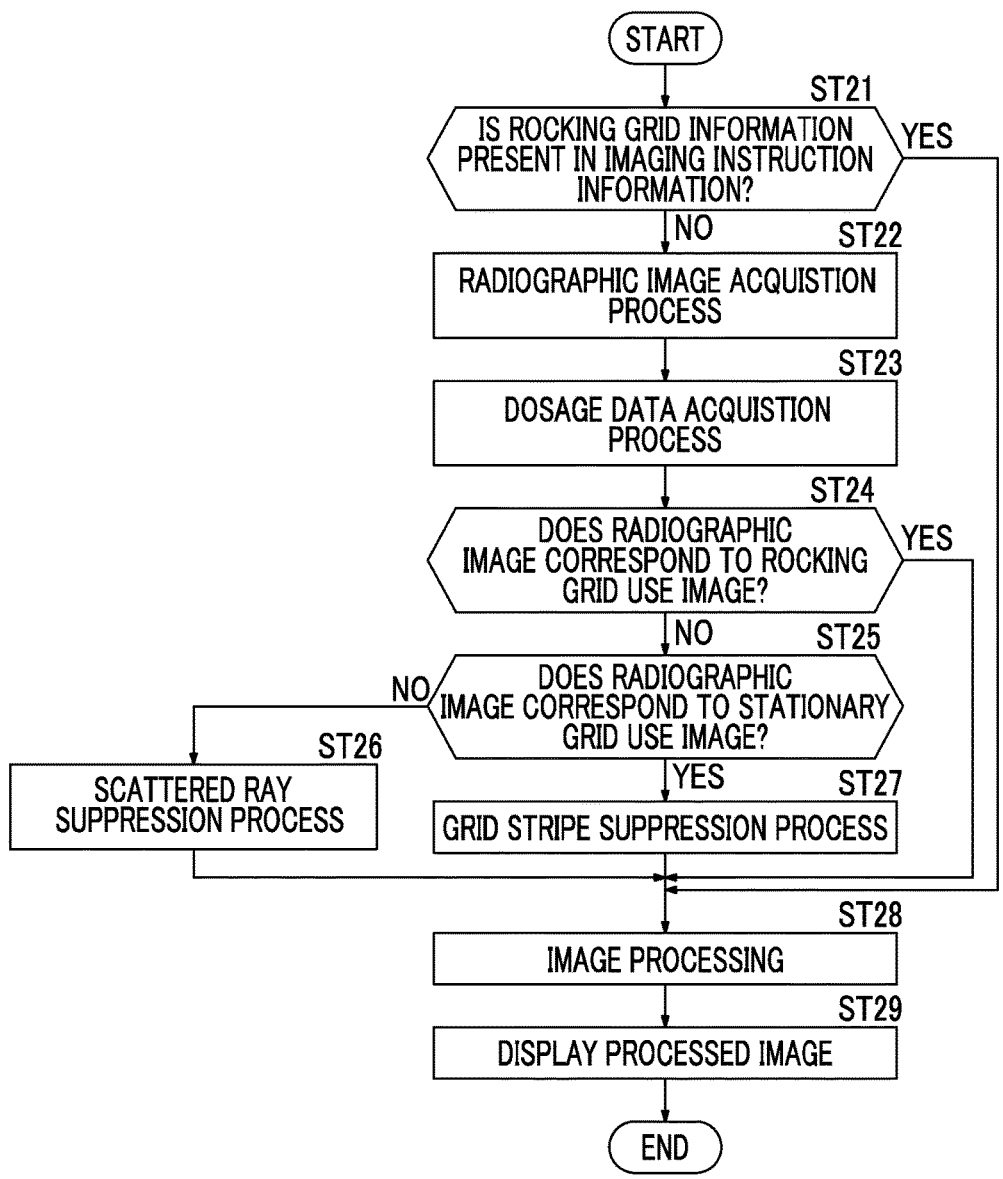
FIG. 11 is a flowchart illustrating a process performed in a third embodiment.

FIG. 11 is a flowchart illustrating a process performed in the third embodiment. Since the third embodiment is different from the first embodiment in that the determining section 43 further has a function of determining a rocking grid use image according to whether rocking grid information indicating whether a radiographic image is captured by rocking a rocking imaging grid is included in imaging instruction information indicating an imaging instruction of the radiographic image, and other functions of the determining section 43, and other components and functions thereof are the same as in the first embodiment, description about the same portions will not be repeated. The flow of processes in an image analysis device according to the third embodiment will be described with reference to FIG. 11.

The "imaging instruction information" refers to information transmitted to an imaging operator from a doctor for instruction of imaging, which includes information for specifying an imaging target and image inspection performed with respect to the imaging target. Thus, there is a possibility that an instruction for rocking a grid for imaging is included in the imaging instruction information. When the imaging instruction information includes information for instructing rocking of the grid, the determining section 43 may obtain rocking grid information with reference to the imaging instruction information. For example, the imaging instruction information includes basic information relating to an imaging target such as a name, gender and age of a patient, an instruction of radiography, an imaging range, an imaging direction, imaging conditions, and the like.

As shown in FIG. 11, first, the determining section 43 acquires imaging instruction information corresponding to a radiographic image, and determines whether rocking grid information indicating whether the radiographic image is captured by rocking a rocking imaging grid is included in the imaging instruction information indicating an imaging instruction of the radiographic image with reference to the imaging instruction information (step ST21). When the imaging instruction information corresponding to the radiographic image includes the rocking grid information, the determining section 43 determines that the radiographic image corresponds to a rocking grid use image (step ST21, Yes). Then, the image processing section 48 sets an image processing parameter for the rocking grid use image with respect to the rocking grid use image and performs necessary image processing to generate a radiographic image G0 which is subjected to the necessary image processing (step ST28). Further, the display controller 49 displays the radiographic image G0 on the display 50 (step ST29).

On the other hand, when the rocking grid information is not included in the imaging instruction information (step ST21, No), the determining section 43 performs the same processes as in ST1 to ST8 of the first embodiment. That is, the image acquisition section 41 acquires a radiographic image corresponding to the acquired dosage data (step ST22), the dosage data acquisition section 42 acquires the dosage data (step ST23), and then, the determining section 43 determines the presence or absence of the first feature of the dosage data based on the dosage data and determines that the radiographic image corresponding to the dosage data having the first feature corresponds to the rocking grid use image (step ST24, Yes). When it is determined that the radiographic image corresponds to the rocking grid use image, the image processing section 48 sets an image processing parameter for the rocking grid use image with respect to the rocking grid use image and performs necessary image processing to generate a radiographic image G0 which is subjected to the image processing (step ST28). Further, the display controller 49 displays the radiographic image G0 on the display 50 (step ST29).

In addition, when it is determined by the determining section 43 that the dosage data does not have the first feature, that is, when it is determined that the radiographic image does not correspond to the rocking grid use image (step ST24, No), the grid stripe detector 45 detects the presence or absence of a grid stripe of the radiographic image, and when the grid stripe is detected by the grid stripe detector 45, the determining section 43 determines that the radiographic image in which the grid stripe is detected is a stationary grid use image (step ST25, Yes). Then, the grid stripe suppressing section 46 performs a grid stripe suppression process with respect to the stationary grid use image (step ST27), and the image processing section 48 sets an image processing parameter for the stationary grid use image with respect to the stationary grid use image which is subjected to the grid stripe suppression process and performs necessary image processing to generate a radiographic image G1 which is subjected to the image processing (step ST28). Further, the display controller 49 displays the radiographic image G1 on the display 50 (step ST29).

Further, when the grid stripe detector 45 detects the presence or absence of the grid stripe of the radiographic image and the grid stripe is not detected by the grid stripe detector 45, the determining section 43 determines that the radiographic image in which the grid stripe is not detected is a grid non-use image (step ST25, No). Further, the scattered ray suppressing section 47 performs a scattered lay suppression process with respect to the grid non-use image (step ST26), and the image processing section 48 sets an image processing parameter for the grid non-use image with respect to the grid non-use image which is subjected to the scattered ray suppression process and performs necessary image processing to generate a radiographic image G2 which is subjected to the image processing (step ST28). Further, the display controller 49 displays the radiographic image G2 on the display 50 (step ST29).

According to the third embodiment, the imaging instruction information is associated with each radiographic image, and the process of determining the rocking grid use image only when the rocking grid information is not acquired by the imaging instruction information using the fact that the imaging instruction information is information including information for specifying an imaging target and image inspection performed with respect to the imaging target is performed. Accordingly, it is possible to achieve a reduction of the calculation load and high speed processing, and to appropriately determine whether a radiographic image is a rocking grid use image.

Further, the rocking grid information which is information indicating whether a radiographic image corresponds to a rocking grid use image acquired by the determining section 43 according to the embodiment of the invention may be utilized for arbitrary processing in an arbitrary device where the rocking grid information is necessary.

In the embodiment of the invention, the grid stripe detector 45, the grid stripe suppressing section 46, the scattered ray suppressing section 47, the image processing section 48, and the display controller 49 are not essential components, and thus, may not be provided. Further, any one of the process of acquiring dosage data (for example, ST1 in FIG. 9) and the process of acquiring a radiographic image corresponding to dosage data (for example, ST2 in FIG. 9) may be preferentially performed, or the processes may be performed at the same time.

In addition, in this embodiment, the console 16 and the radiographic image processing device 14 are provided as separate devices, but the invention is not limited thereto. The console 16 and the radiographic image processing device 14 may be combined as a single device, and the components and functions of the console 16 and the radiographic image processing device 14 may be configured by a single console.

Further, in each embodiment, the scattered ray suppression process is performed using the radiographic image acquired in the radiation imaging system 10 that captures the radiographic image of the photographic subject using the radiation detector 26, but even in a case where radiographic image information of a photographic subject is accumulatively recorded on a storage fluorescent sheet which is a radiation detector and a radiographic image acquired from the storage fluorescent sheet by photoelectric reading is used as disclosed in JP1996-266529A (JP-H8-266529A), JP1997-24039A (JP-H9-24039A), or the like, the invention may be applied.

Furthermore, the process of removing a stripe pattern due to a grid may be performed by various methods capable of removing the stripe pattern due to the grid. For example, a method disclosed in JP2012-203504A, or the like may be used.

The above-described embodiments are merely examples, and thus, the entire description should not be used to construe a technical scope of the invention to be limited. Embodiments of the invention are not limited to the above-described examples (first to third embodiments, and other modification examples and application examples), and the invention includes various combinations of the respective components of the respective embodiments. Further, the embodiments of the invention include various modifications conceivable by those skilled in the art. That is, various additions, modifications, and partial omissions may be made in a range without departing from the conceptual idea and spirit of the invention derived from the content defined by claims and equivalents thereof Further, various modifications performed in a range without departing from the spirit of the invention with respect to the system configurations, the hardware configurations, the processing flows, the module configurations, the user interfaces, the specific processing contents, and the like in the above-described embodiments are also included in the technical scope of the invention. For example, a part or the entirety of the components of the image analysis device may be configured by a single workstation, or may be configured by one or more workstations, a server, and a storage device which are connected to each other through a network.

What is claimed is:

1. An image analysis device comprising:
a radiographic image acquisition section that acquires a radiographic image acquired by radiography;
a dosage data acquisition section that acquires dosage data indicating, in a time-series manner, a dosage of radiation rays exposed to a specific position in an imaging area corresponding to the radiographic image in a specific period including an imaging period of the radiographic image; and
a determining section that determines whether the dosage data has a first feature indicating a dosage variation as a plurality of radiation absorbing bodies and a radiation transmitting body disposed between adjacent radiation absorbing bodies pass through a space between the specific position and a radiation source used for the radiography, and determines that the radiographic image corresponding to the dosage data determined to have the first feature is a rocking grid use image captured by rocking a rocking imaging grid for removing scattered rays.

2. The image analysis device according to claim 1,
wherein the determining section determines whether the dosage data has the first feature, using a feature that the dosage data has adjacent sine wave shapes having a uniform amplitude as the first feature.

3. The image analysis device according to claim 2,
wherein the determining section determines whether the dosage data has the first feature using a feature that the dosage data alternately has a positive maximum value due to passage of each radiation transmitting body and a minimum value which is zero or greater due to passage of each radiation absorbing body at a uniform interval as the first feature.

4. The image analysis device according to claim 2,
wherein the determining section determines that the radiographic image corresponding to the dosage data determined not to have the first feature is any one of a stationary grid use image captured with a stationary imaging grid for removing scattered rays being stationary and a grid non-use image captured with the grid for removing the scattered rays not being used.

5. The image analysis device according to claim 2,
wherein the determining section determines whether the radiographic image has a second feature indicating that the radiographic image includes an image of a stationary imaging grid, determines that the radiographic image determined to have the second feature is a stationary grid use image, and determines that the radiographic image corresponding to the dosage data determined not to have the first feature and determined not to have the second feature is a grid non-use image.

6. The image analysis device according to claim 2,
wherein the determining section determines whether rocking grid information indicating that the radiographic image is captured by rocking the rocking imaging grid is included in imaging instruction information indicating an imaging instruction of the radiographic image, determines the rocking grid use image in a case where it is determined that the rocking grid information is included in the imaging instruction information based on the rocking grid information of the imaging instruction information, and determines the rocking grid use image by determining whether the dosage data has the first feature in a case where it is determined that the rocking grid information is not included in the imaging instruction information.

7. The image analysis device according to claim 1,
wherein the determining section determines whether the dosage data has the first feature, using a feature that the dosage data alternately has a positive maximum value due to passage of each radiation transmitting body and a minimum value which is zero or greater due to passage of each radiation absorbing body at a uniform interval as the first feature.

8. The image analysis device according to claim 7,
wherein the determining section determines that the radiographic image corresponding to the dosage data determined not to have the first feature is any one of a stationary grid use image captured with a stationary imaging grid for removing scattered rays being stationary and a grid non-use image captured with the grid for removing the scattered rays not being used.

9. The image analysis device according to claim 7,
wherein the determining section determines whether the radiographic image has a second feature indicating that the radiographic image includes an image of a stationary imaging grid, determines that the radiographic image determined to have the second feature is a stationary grid use image, and determines that the radiographic image corresponding to the dosage data determined not to have the first feature and determined not to have the second feature is a grid non-use image.

10. The image analysis device according to claim 7, wherein the determining section determines whether rocking grid information indicating that the radiographic image is captured by rocking the rocking imaging grid is included in imaging instruction information indicating an imaging instruction of the radiographic image, determines the rocking grid use image in a case where it is determined that the rocking grid information is included in the imaging instruction information based on the rocking grid information of the imaging instruction information, and determines the rocking grid use image by determining whether the dosage data has the first feature in a case where it is determined that the rocking grid information is not included in the imaging instruction information.

11. The image analysis device according to claim 1, wherein the determining section determines that the radiographic image corresponding to the dosage data determined not to have the first feature is any one of a stationary grid use image captured with a stationary imaging grid for removing scattered rays being stationary and a grid non-use image captured with the grid for removing the scattered rays not being used.

12. The image analysis device according to claim 11, wherein the determining section determines whether the radiographic image has a second feature indicating that the radiographic image is an image of the stationary imaging grid, determines that the radiographic image determined to have the second feature is a stationary grid use image, and determines that the radiographic image corresponding to the dosage data determined not to have the first feature and determined not to have the second feature is the grid non-use image.

13. The image analysis device according to claim 1, wherein the determining section determines whether the radiographic image has a second feature indicating that the radiographic image includes an image of a stationary imaging grid, determines that the radiographic image determined to have the second feature is a stationary grid use image, and determines that the radiographic image corresponding to the dosage data determined not to have the first feature and determined not to have the second feature is a grid non-use image.

14. The image analysis device according to claim 13, further comprising:
a grid stripe suppressing section that suppresses a frequency component corresponding to the image indicating the stationary imaging grid included in the stationary grid use image from the stationary grid use image.

15. The image analysis device according to claim 14, further comprising:
a scattered ray suppressing section that performs a scattered ray component suppression process of generating a scattered ray image indicating a scattered ray component in each position of the grid non-use image from the grid non-use image, and subtracting the scattered ray image from the grid non-use image.

16. The image analysis device according to claim 13, further comprising:
a scattered ray suppressing section that performs a scattered ray component suppression process of generating a scattered ray image indicating a scattered ray component in each position of the grid non-use image from the grid non-use image, and subtracting the scattered ray image from the grid non-use image.

17. The image analysis device according to claim 1, wherein the determining section determines whether rocking grid information indicating that the radiographic image is captured by rocking the rocking imaging grid is included in imaging instruction information indicating an imaging instruction of the radiographic image, determines the rocking grid use image in a case where it is determined that the rocking grid information is included in the imaging instruction information based on the rocking grid information of the imaging instruction information, and determines the rocking grid use image by determining whether the dosage data has the first feature in a case where it is determined that the rocking grid information is not included in the imaging instruction information.

18. The image analysis device according to claim 1, wherein the determining section adds determination information indicating whether it is determined that the radiographic image is the rocking grid use image as additional information with respect to the radiographic image.

19. An image analysis method that is executed in the image analysis device according to claim 1, comprising the steps of:
acquiring the radiographic image acquired by radiography;
acquiring dosage data indicating, in a time-series manner, the dosage of radiation rays exposed to the specific position in the imaging area corresponding to the radiographic image in the specific period including the imaging period of the radiographic image; and
determining whether the dosage data has the first feature indicating the dosage variation as the plurality of radiation absorbing bodies and the radiation transmitting body disposed between adjacent radiation absorbing bodies pass through the space between the specific position and the radiation source used for the radiography, and determining that the radiographic image corresponding to the dosage data determined to have the first feature is the rocking grid use image captured by rocking the rocking imaging grid for removing scattered rays.

20. A non-transitory computer-readable recording medium that stores an image analysis program that causes a computer using the image analysis device according to claim 1 to execute a routine comprising the steps of:
acquiring the radiographic image acquired by radiography;
acquiring dosage data indicating, in a time-series manner, the dosage of radiation rays exposed to the specific position in the imaging area corresponding to the radiographic image in the specific period including the imaging period of the radiographic image; and
determining whether the dosage data has the first feature indicating the dosage variation as the plurality of radiation absorbing bodies and the radiation transmitting body disposed between adjacent radiation absorbing bodies pass through the space between the specific position and the radiation source used for the radiography, and determining that the radiographic image corresponding to the dosage data determined to have the first feature is the rocking grid use image captured by rocking the rocking imaging grid for removing scattered rays.

* * * * *